(12) United States Patent
Tsunoda et al.

(10) Patent No.: US 9,119,800 B2
(45) Date of Patent: Sep. 1, 2015

(54) HIG2 AND URLC10 EPITOPE PEPTIDE AND VACCINES CONTAINING THE SAME

(75) Inventors: Takuya Tsunoda, Kanagawa (JP); Ryuji Ohsawa, Kanagawa (JP); Sachiko Yoshimura, Kanagawa (JP)

(73) Assignee: OncoTherapy Science, Inc., Kanagawa (JP)

( * ) Notice: Subject to any disclaimer, the term of this patent is extended or adjusted under 35 U.S.C. 154(b) by 1188 days.

(21) Appl. No.: 13/059,618

(22) PCT Filed: Aug. 14, 2009

(86) PCT No.: PCT/JP2009/003897
§ 371 (c)(1),
(2), (4) Date: Jun. 9, 2011

(87) PCT Pub. No.: WO2010/021112
PCT Pub. Date: Feb. 25, 2010

(65) Prior Publication Data
US 2011/0243973 A1 Oct. 6, 2011

Related U.S. Application Data

(60) Provisional application No. 61/089,972, filed on Aug. 19, 2008.

(51) Int. Cl.
*A61K 39/385* (2006.01)
*A61K 39/00* (2006.01)
*C07K 14/725* (2006.01)
*A61K 38/00* (2006.01)

(52) U.S. Cl.
CPC ......... *A61K 39/0011* (2013.01); *C07K 14/7051* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 7,727,714 | B2 | 6/2010 | Nakamura et al. |
| 7,847,060 | B2 | 12/2010 | Tahara et al. |
| 2002/0128201 | A1 | 9/2002 | Itoh |
| 2003/0232350 | A1 | 12/2003 | Afar et al. |
| 2006/0024692 | A1 | 2/2006 | Nakamura et al. |
| 2007/0014787 | A1 | 1/2007 | Ruben |
| 2007/0015271 | A1 | 1/2007 | Rosen et al. |
| 2008/0286313 | A1 | 11/2008 | Itoh |
| 2008/0306243 | A1 | 12/2008 | Miyakawa et al. |
| 2009/0175844 | A1 | 7/2009 | Nakamura et al. |
| 2010/0040641 | A1 | 2/2010 | Tsunoda et al. |
| 2010/0204060 | A1 | 8/2010 | Nakamura et al. |
| 2010/0291091 | A1 | 11/2010 | Nakamura et al. |
| 2011/0027302 | A1 | 2/2011 | Tahara et al. |
| 2011/0200626 | A1 | 8/2011 | Tsunoda et al. |
| 2012/0014996 | A1 | 1/2012 | Nakamura et al. |
| 2012/0021945 | A1 | 1/2012 | Nakamura et al. |

FOREIGN PATENT DOCUMENTS

| | | |
|---|---|---|
| AU | 2008/218463 A1 | 8/2008 |
| EP | 1207199 A1 | 5/2002 |
| EP | 1854473 A1 | 11/2007 |
| EP | 2030984 A1 | 3/2009 |
| JP | 2006-500949 A | 1/2006 |
| JP | 2007-246451 A | 9/2007 |
| JP | 2010-519176 A | 6/2010 |
| RU | 2451521 C2 | 5/2012 |
| TW | 2008/44111 A | 11/2008 |
| WO | WO 01/11044 A1 * | 2/2001 |
| WO | WO 01/23426 A2 | 4/2001 |
| WO | WO 02/30268 A2 | 4/2002 |
| WO | WO 2004/031413 A2 | 4/2004 |
| WO | 2005/016962 A2 | 2/2005 |
| WO | 2005/019258 A2 | 3/2005 |
| WO | 2005/019475 A2 | 3/2005 |
| WO | WO 2005/019475 A2 | 3/2005 |
| WO | WO 2005/123122 A1 | 12/2005 |
| WO | WO 2006/085684 A2 | 8/2006 |
| WO | WO 2006/090810 A2 * | 8/2006 |
| WO | WO 2006/093337 A1 | 9/2006 |
| WO | 2007/013575 A2 | 2/2007 |
| WO | WO 2007/029778 A1 | 3/2007 |
| WO | 2008/102557 A1 | 8/2008 |
| WO | WO 2008/102557 A1 | 8/2008 |
| WO | WO 2009/016691 A1 | 2/2009 |

OTHER PUBLICATIONS

Togashi et al (Cancer Res, 2005, 65(11): 4817-4826).*
Kantakamalakul et al (AIDS Research and Human Reteroviruses, 2006, 22(12): 1271-1282).*
U.S. Appl. No. 14/274,373, filed May 9, 2014, 123 pages.
Imai, et al., "Identification of Lck-Derived Peptides Capable of Inducing HLA-A2-Restricted and Tumor Specific CTLS in Cancer Patients with Distant Metastases," *Int J Cancer*, vol. 94(2), pp. 237-242 (Oct. 15, 2001).
U.S. Appl. No. 13/536,327, filed Jun. 28, 2012, 204 pgs.
Boon, "Toward a Genetic Analysis of Tumor Rejection Antigens," *Adv Cancer Res.*, vol. 58, pp. 177-210 (1992).
Burgess, et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," *J Cell Biol.*, vol. 111(5 Pt 1), pp. 2129-2138 (Nov. 1990).
Dionne, et al., "Functional characterization of CTL against gp100 altered peptide ligands," *Cancer Immunol Immunother.*, vol. 52(4), pp. 199-206 (Apr. 2003, Epub Feb. 18, 2003).
Dionne, et al., "Her-2/*neu* altered peptide ligand-induced CTL responses: implications for peptides with increased HLA affinity and T-cell-receptor interaction," *Cancer Immunol Immunother.*, vol. 53(4), pp. 307-314 (Apr. 2004, Epub Nov. 5, 2003).

(Continued)

*Primary Examiner* — Sean Aeder
(74) *Attorney, Agent, or Firm* — Kilpatrick Townsend & Stockton LLP

(57) ABSTRACT

The present invention provides a pharmaceutical agent or composition containing one or more peptides having the amino acid sequence of SEQ ID NO: 1 or 2, or one or more polynucleotides encoding such a peptide formulated for the treatment and/or prevention of cancer in a subject whose HLA-A antigen is HLA-A0206. Furthermore, the present invention provides a method of inducing CTL and antigen-presenting cells using such peptides, polynucleotides or pharmaceutical agents.

4 Claims, 6 Drawing Sheets

(56) References Cited

OTHER PUBLICATIONS

Falk, et al., "Allele-specific motifs revealed by sequencing of self-peptides eluted from MHC molecules," *Nature*, vol. 351(6324), pp. 290-296 (May 23, 1991).
Harada, et al., "Kinesin superfamily protein-derived peptides with the ability to induce glioma-reactive cytotoxic T Lymphocytes in human leukocyte antigen-A24+ glioma patients," *Oncol Rep.*, vol. 17(3), pp. 629-636 (Mar. 2007).
Hoffmann, et al., "The Ability of Variant Peptides to Reverse the Nonresponsiveness of T Lymphocytes to the Wild-Type Sequence p53$_{264-272}$ Epitope," *J Immunol.*, vol. 168(3), pp. 1338-1347 (Feb. 1, 2002).
Kondo, et al., "Prominent Roles of Secondary Anchor Residues in Peptide Binding to HLA-A24 Human Class I Molecules," *J Immunol.*, vol. 155(9), pp. 4307-4312 (Nov. 1, 1995).
Kubo, et al., "Definition of Specific Peptide Motifs for Four Major HLA-A Alleles," *J Immunol.*, vol. 152(8), pp. 3913-3924 (Apr. 15, 1994).
Lazar, et al., "Transforming Growth Factor α: Mutation of Aspartic Acid 47 and Leucine 48 Results in Different Biological Activities," *Mol Cell Biol.*, vol. 8(3), pp. 1247-1252 (Mar. 1988).
Mizukami, et al., "Detection of novel cancer-testis antigen-specific T-cell responses in TIL, regional lymph nodes, and PBL in patients with esophageal squamous cell carcinoma," *Cancer Sci.*, vol. 99(7), pp. 1448-1454 (Jul. 2008, Epub Apr. 30, 2008).
Parker, et al., "Scheme for Ranking Potential HLA-A2 Binding Peptides Based on Independent Binding of Individual Peptide Side-Chains," *J Immunol.*, vol. 152(1), pp. 163-175 (Jan. 1, 1994).
Rammensee, et al., "MHC ligands and peptide motifs: first listing," *Immunogenetics*, vol. 41(4), pp. 178-228 (1995).
Schueler-Furman, et al., "Structure-based prediction of binding peptides to MHC class I molecules: Application to a broad range of MHC alleles," *Protein Sci.*, vol. 9(9), pp. 1838-1846 (Sep. 2000).
Sidney, et al., "Majority of Peptides Binding HLA-A *0201 With High Affinity Crossreact With Other A2-Supertype Molecules," *Hum Immunol.*, vol. 62(11), pp. 1200-1216 (Nov. 2001).
Suda, et al., "Identification of *secernin* 1 as a novel immunotherapy target for gastric cancer using the expression profiles of cDNA microarray," *Cancer Sci.*, vol. 97(5), pp. 411-419 (May 2006).
Zaremba, et al., "Identification of an Enhancer Agonist Cytotoxic T Lymphocytes Peptide from Human Carcinoembryonic Antigen," *Cancer Res.*, vol. 57(20), pp. 4570-4577 (Oct. 15, 1997).
Zhu, et al., "Improving MHC binding peptide prediction by incorporating binding data of auxiliary MHC molecules," *Bioinformatics*, vol. 22(13), pp. 1648-1655 (Jul. 1, 2006, Epub Apr. 13, 2006).
U.S. Appl. No. 13/744,354, filed Jan. 17, 2013, 124 pages.
Adams, H-P., et al., "Prediction of binding to MHC class I molecules," *Journal of Immunological Methods*, vol. 185(2), pp. 181-190 (Sep. 25, 1995).
Belli, F., et al., "Vaccination of Metastatic Melanoma Patients with Autologous Tumor-Derived Heat Shock Protein gp96-Peptide Complexes: Clinical and Immunologic Findings," *Journal of Clinical Oncology*, vol. 20(20), pp. 4169-4180 (Oct. 15, 2002).
Boon, T., "Tumor Antigens Recognized by Cytolytic T Lymphocytes: Present Perspectives for Specific Immunotherapy," *Int. J. Cancer*, vol. 54(2), pp. 177-180 (May 8, 1993).
Boon, T., et al., "Human Tumor Antigens Recognized by T Lymphocytes," *J. Exp. Med.*, vol. 183(3), pp. 725-729 (Mar. 1, 1996).
Butterfield, L., et al., "Generation of Human T-cell Responses to an HLA-A2.1-restricted Peptide Epitope Derived from α-Fetoprotein," *Cancer Research*, vol. 59(13), pp. 3134-3142 (Jul. 1, 1999).
Coulie, P., et al., "Cytolytic T-cell responses of cancer patients vaccinated with a MAGE antigen," *Immunological Reviews*, vol. 188, pp. 33-42 (Oct. 2002).
De Nooij-Van Dalen, A., et al., "Characterization of the Human LY-6 Antigens, the Newly Annotated Member LY-6K Included, as Molecular Markers for Head-and-Neck Squamous Cell Carcinoma," *Int. J. Cancer*, vol. 103(6), pp. 768-774 (Mar. 1, 2003).

Denko, N., et al., "Epigenetic Regulation of Gene Expression in Cervical Cancer Cells by the Tumor Microenvironment," *Clinical Cancer Research*, vol. 6(2), pp. 480-487 (Feb. 2000).
Fujie, T., et al., "A *MAGE*-1-Encoded HLA-A24-Binding Synthetic Peptide Induces Specific Anti-Tumor Cytotoxic T Lymphocytes," *Int. J. Cancer*, vol. 80(2), pp. 169-172 (Jan. 18, 1999).
Harris, C., "Structure and Function of the p53 Tumor Suppressor Gene: Clues for Rational Cancer Therapeutic Strategies," *Journal of the National Cancer Institute*, vol. 88(20), pp. 1442-1455 (Oct. 16, 1996).
Ishikawa, N., et al., "Cancer-Testis Antigen Lymphocyte Antigen 6 Complex Locus K Is a Serologic Biomarker and a Therapeutic Target for Lung and Esophageal Carcinomas," *Cancer Research*, vol. 67(24), pp. 11601-11611 (Dec. 15, 2007).
Jiang, Y., et al., "Gene Expression Profiling in a Renal Cell Carcinoma Cell Line: Dissecting VHL and Hypoxia-Dependent Pathways," *Molecular Cancer Research*, vol. 1(6), pp. 453-462 (Apr. 2003).
Katagiri, T., et al., "Hypoxia-inducible protein 2 (HIG2), a novel diagnostic marker for renal cell carcinoma (RCC) and potential target for molecular therapy," *Proceedings of the American Association for Cancer Research*, vol. 47, p. 304, Abst. # 1289 (Apr. 2006).
Kikuchi, M., et al., "Identification of a SART-1-Derived Peptide Capable of Inducing HLA-A24-Restricted and Tumor-Specific Cytotoxic T Lymphocytes," *Int. J. Cancer*, vol. 81(3), pp. 459-466 (May 5, 1999).
Kono, K., et al., "Vaccination with multiple peptides derived from novel cancer-testis antigens can induce specific T-cell responses and clinical responses in advanced esophageal cancer," *Cancer Sci.*, vol. 100(8), pp. 1502-1509 (Aug. 2009).
Latif, F., et al., "Identification of the von Hippel-Lindau Disease Tumor Suppressor Gene," *Science*, vol. 260(5112), pp. 1317-1320 (May 28, 1993).
Lee, K., et al., "Allelic and haplotypic diversity of *HLA-A, -B, -C, -DRB1*, and *-DQB1* genes in the Korean population," *Tissue Antigens*, vol. 65(5), pp. 437-447 (May 2005).
Oiso, M., et al., "A Newly Identified *MAGE-3*-Derived Epitope Recognized by HLA-A24-Restricted Cytotoxic T Lymphocytes," *Int. J. Cancer*, vol. 81(3), pp. 387-394 (May 5, 1999).
Rosenberg, S., et al., "Cancer immunotherapy: moving beyond current vaccines," *Nat. Med.*, vol. 10(9), pp. 909-915 (Sep. 2004).
Suda, T., et al., "Identification of human leukocyte antigen-A24-restricted epitope pepeides derived from gene products upregulated in lung and esophageal cancers as novel targets for immunotherapy," *Cancer Science*, vol. 98(11), pp. 1803-1808 (Nov. 2007).
Tahara, H., Slides for the symposium of the Japanese Cancer Association, 6 pgs. (Feb. 7, 2006).
Tanaka, F., et al., "Induction of Antitumor Cytotoxic T Lymphocytes with a MAGE-3-encoded Synthetic Peptide Presented by Human Leukocytes Antigen-A24," *Cancer Research*, vol. 57(20), pp. 4465-4468 (Oct. 15, 1997).
Togashi, A., et al., "A novel potential molecular target for treatment of renal cell carcinoma (RCC)," *Proceedings of the American Association for Cancer Research*, vol. 45, pp. 481-482, Abst. # 2093 (Mar. 2004).
Togashi, A., et al., "Identification of novel therapeutic target and tumor marker for renal cell carcinoma," *Proceedings of the 63$^{rd}$ Annual meeting of the Japanese Cancer Association*, p. 215, Abst. # W-174 (Aug. 25, 2004).
Togashi, A., et al., "Screening for novel therapeutic target and tumor marker of renal cell carcinoma using cDNA microarray," *Proceedings of the 62$^{nd}$ Annual Meeting of the Japanese Cancer Association*, p. 216, Abst. # 3002-OA (Aug. 25, 2003).
Togashi, A., et al., "Functional analysis and clinical diagnostic trail of C6776, a novel therapeutic target and tumor marker for renal cell carcinoma," *Proceedings of the 64$^{th}$ Annual Meeting of the Japanese Cancer Association*, p. 443, Abst. # W-716 (Aug. 15, 2005).
Togashi, A., et al., "Hypoxia-Inducible Protein 2 (*HIG2*), a Novel Diagnostic Marker for Renal Cell Carcinoma and Potential Target for Molecular Therapy," *Cancer Research*, vol. 65(11), pp. 4817-4826 (Jun. 1, 2005).

(56) References Cited

OTHER PUBLICATIONS

Togashi, A., et al., "Hypoxia-Inducible Protein 2 (*HIG2*), a Novel Diagnostic Marker for Renal Cell Carcinoma and Potential Target for Molecular Therapy," *Journal of Urology*, vol. 175, p. 1272 (Apr. 2006).

Tsunoda, T., et al., "Phase I clinical trial of epitope peptides based vaccine with novel tumor associate antigen, RNF43 and URLC10, found by genome-wide exploration using cDNA Microarray Profiling (GET-MAP) against colorectal cancer and esophageal cancer patients," *Annual Report 2005*, Institute of Medical Science, The University of Tokyo, p. 247-248 (Mar. 1, 2006).

Van Der Burg, S., et al., "Immunogenicity of Peptides Bound to MHC Class I Molecules Depends on the MHC-Peptide Complex Stability," *Journal of Immunology*, vol. 156(9), pp. 3308-3314 (May 1, 1996).

Vissers, J., et al., "The Renal Cell Carcinoma-associated Antigen G250 Encodes a Human Leukocyte Antigen (HLA)-A2.1-restricted Epitope Recognized by Cytotoxic T Lymphocytes," *Cancer Research*, vol. 59(21), pp. 5554-5559 (Nov. 1, 1999).

Wiesener, M., et al., Constitutive Activation of Hypoxia-inducible Genes Related to Overexpression of Hypoxia-inducible Factor-1α in Clear Cell Renal Carcinomas, *Cancer Research*, vol. 61(13), pp. 5215-5222 (Jul. 1, 2001).

EBI Accession No. UNIPROT: Q5ZED4, Version 73, 5 pgs. (last modified Sep. 21, 2011, downloaded Jan. 13, 2012).

U.S. Appl. No. 13/464,831, filed May 4, 2012, 163 pages.

Ishizaki et al., "Inhibition of Tumor Growth with Antiangiogenic Cancer Vaccine Using Epitope Peptides Derived from Human Vascular Endothelial Growth Factor Receptor 1", *Clin Cancer Res.*, vol. 12, No. 19, pp. 5841-5849 (2006).

Murray et al., *Biochemistry of Human*, Moscow: Mir., chapter 4, p. 34 (1993), with English translation, 5 pages.

U.S. Appl. No. 14/079,144, filed Nov. 13, 2013, 159 pages.

U.S. Appl. No. 11/913,147, filed Oct. 30, 2007, 134 pages.

Seki et al., "HLA-A Locus-Restricted and Tumor-Specific CTLs in Tumor-Infiltrating Lymphocytes of Patients with Non-Small Cell Lung Cancer", *Cellular Immunology*, vol. 175, pp. 101-110 (1997).

U.S. Appl. No. 14/413,416, filed Jan. 7, 2015, 175 pages.

\* cited by examiner

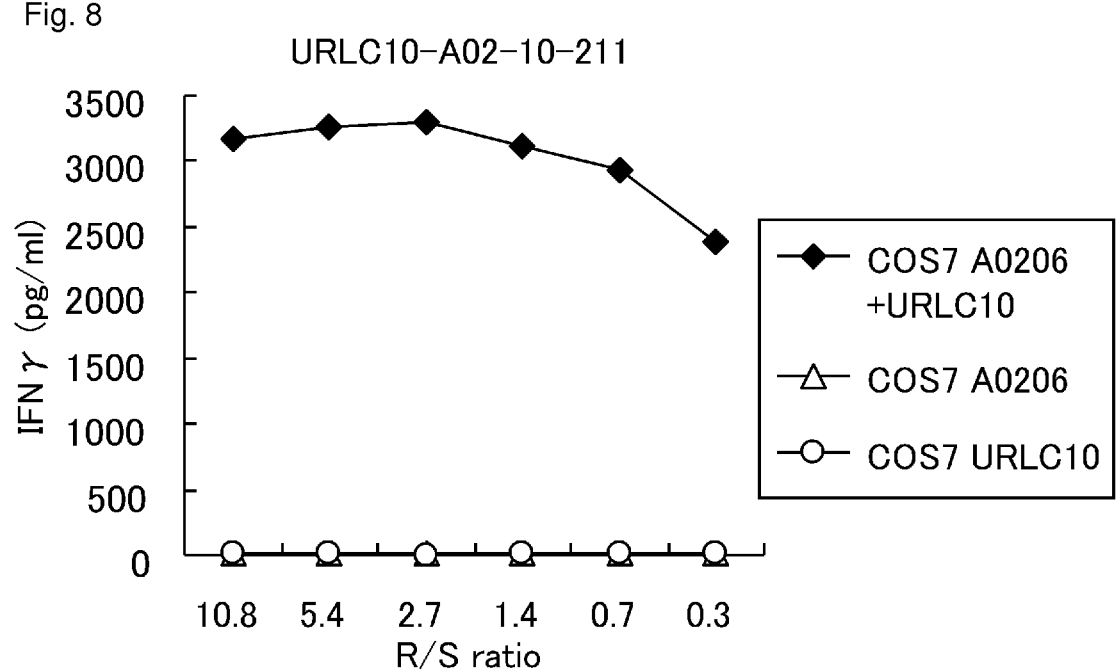

HIG2 AND URLC10 EPITOPE PEPTIDE AND VACCINES CONTAINING THE SAME

PRIORITY

The present application is a U.S. National Stage Application of PCT/JP2009/003897, filed Aug. 14, 2009, which claims the benefit of U.S. Provisional Application No. 61/089,972, filed on Aug. 19, 2008, the entire contents of which are incorporated by reference herein in their entirety.

TECHNICAL FIELD

1. Technical Field

The present invention relates to the field of biological science, more specifically to the field of cancer therapy. In particular, the present invention relates to novel peptides that are extremely effective as cancer vaccines, and drugs for treating and preventing tumors.

2. Background Art

It has been demonstrated that CD8 positive CTLs recognize epitope peptides derived from the tumor-associated antigens (TAAs) found on major histocompatibility complex (MHC) class I molecule, and then kill the tumor cells. Since the discovery of the melanoma antigen (MAGE) family as the first example of TAAs, many other TAAs have been discovered, primarily through immunological approaches (NPL 1: Boon T, Int J Cancer 1993 May 8, 54(2): 177-80; NPL 2: Boon T & van der Bruggen P, J Exp Med 1996 Mar. 1, 183(3): 725-9). Some of the TAAs are now currently undergoing clinical development as immunotherapeutic targets.

Identification of new TAAs capable of inducing potent and specific anti-tumor immune responses, warrants further development and clinical application of peptide vaccination strategies for various types of cancer (NPL 3: Harris C C, J Natl Cancer Inst 1996 Oct. 16, 88(20): 1442-55; NPL 4: Butterfield L H et al., Cancer Res 1999 Jul. 1, 59(13): 3134-42; NPL 5: Vissers J L et al., Cancer Res 1999 Nov. 1, 59(21): 5554-9; NPL 6: van der Burg S H et al., J Immunol 1996 May 1, 156(9): 3308-14; NPL 7: Tanaka F et al., Cancer Res 1997 Oct. 15, 57(20): 4465-8; NPL 8: Fujie T et al., Int J Cancer 1999 Jan. 18, 80(2): 169-72; NPL 9: Kikuchi M et al., Int J Cancer 1999 May 5, 81(3): 459-66; NPL 10: Oiso M et al., Int J Cancer 1999 May 5, 81(3): 387-94). To date, there have been several reports of clinical trials using these tumor-associated antigen derived peptides. Unfortunately, only a low objective response rate has been observed in these cancer vaccine trials so far (NPL 11: Belli F et al., J Clin Oncol 2002 Oct. 15, 20(20): 4169-80; NPL 12: Coulie P G et al., Immunol Rev 2002 October, 188: 33-42; NPL 13: Rosenberg S A et al., Nat Med 2004 September, 10(9): 909-15).

There are several type of HLA-A in the world. Of the known HLA genotypes, genotypes of HLA-A0201, HLA-A0206, HLA-A1101, HLA-A2402, HLA-A2601, HLA-A3101 and HLA-A3303 are known to have a higher frequency of expression than other types (NPL 14: Lee K W, et al., Tissue Antigens 2005: 65: 437-447). However, each genotype has a different amino acid sequence and different affinity against epitope peptide (NPL 15: Journal of Immunological Methods, (1995), Vol. 185, pp. 181-190). For example, the amino acid residue of the alpha 1-domain of the HLA-A0206 genotype differs from that of the HLA-A0201 genotype (i.e., the tyrosine residue at 33rd amino acid of SEQ ID NO: 8 is replaced with phenylalanine). Given these differences, it is unlikely that an HLA-A0201 restricted epitope peptide will be useful for a patient who possesses HLA-A0206 genotype. Accordingly, a peptide useful for various types of patients remains a goal in the art.

HIG2 (hypoxia-inducible gene 2) and URLC10 (also, referred as LY6K; lymphocyte antigen 6 complex, locus K) are confirmed to be up-regulated in several cancer tissues such as renal cancer and lung cancer by microarray analysis (PTL 1: WO2005/019475, PTL 2: WO2004/031413). Accordingly, HIG2 and URLC10 are interesting targets for cancer immunotherapy and CTL inducing epitope peptides derived therefrom are sought by those in the art.

CITATION LIST

Non Patent Literature

[NPL 1]: Boon T, Int J Cancer 1993 May 8, 54(2): 177-80
[NPL 2]: Boon T & van der Bruggen P, J Exp Med 1996 Mar. 1, 183(3): 725-9
[NPL 3]: Harris C C, J Natl Cancer Inst 1996 Oct. 16, 88(20): 1442-55
[NPL 4]: Butterfield L H et al., Cancer Res 1999 Jul. 1, 59(13): 3134-42
[NPL 5]: Vissers J L et al., Cancer Res 1999 Nov. 1, 59(21): 5554-9
[NPL 6]: van der Burg S H et al., J Immunol 1996 May 1, 156(9): 3308-14
[NPL 7]: Tanaka F et al., Cancer Res 1997 Oct. 15, 57(20): 4465-8
[NPL 8]: Fujie T et al., Int J Cancer 1999 Jan. 18, 80(2): 169-72
[NPL 9]: Kikuchi M et al., Int J Cancer 1999 May 5, 81(3): 459-66
[NPL 10]: Oiso M et al., Int J Cancer 1999 May 5, 81(3): 387-94
[NPL 11]: Belli F et al., J Clin Oncol 2002 Oct. 15, 20(20): 4169-80
[NPL 12]: Coulie P G et al., Immunol Rev 2002 October, 188: 33-42
[NPL 13]: Rosenberg S A et al., Nat Med 2004 September, 10(9): 909-15
[NPL 14]: Lee K W, et al., Tissue Antigens 2005: 65: 437-447
[NPL 15]: Journal of Immunological Methods, (1995), Vol. 185, pp. 181-190

Patent Literature

[PTL 1]: WO2005/019475
[PTL 2]: WO2004/031413

SUMMARY OF INVENTION

The present invention is based in part on the discovery of a new application of two peptides, which have an amino acid sequence shown in SEQ ID NO: 1 or SEQ ID NO: 2. In the context of the present invention, peripheral blood mononuclear cells (PBMCs) obtained from a healthy donor were stimulated with candidate peptides derived from HIG2 or URLC10. CTLs that specifically recognize HLA-A0206 positive target cells pulsed with the respective candidate peptides were established, and HLA-A0206 restricted epitope peptides that can induce potent and specific immune responses against HIG2 or URLC10 presented on the surface of target cells were identified.

Accordingly, it is an object of the present invention to provide peptides having CTL inducibility as well as an amino acid sequence of SEQ ID NOs: 1 or 2. In addition, the present invention contemplates the use of modified peptides, wherein one, two or more amino acids are substituted, deleted, inserted and/or added, so long as the resulting modified peptides retain the CTL inducibility of the original peptide.

When administered to a subject whose HLA antigen is HLA-A0206, the present peptides are presented on the surface of antigen-presenting cells and then induce CTLs targeting the respective peptides. Therefore, it is an object of the present invention to provide antigen-presenting cells and exosomes that present any of the present peptides with HLA-A0206 antigen, as well as methods for inducing antigen-presenting cells.

An anti-tumor immune response is induced by the administration of the present HIG2 or URLC10 polypeptides or polynucleotide encoding the polypeptides, as well as exosomes and antigen-presenting cells which present the HIG2 or URLC10 polypeptides. Therefore, it is yet another object of the present invention to provide pharmaceutical agents containing the polypeptides or polynucleotides encoding them, as well as the exosomes and antigen-presenting cells as their active ingredients which are intended for the administration to a subject whose HLA antigen is HLA-A0206. The pharmaceutical agents of the present invention find use as vaccines.

Moreover, it is a further object of the present invention to provide methods for the treatment and/or prophylaxis of (i.e., prevention) cancers (tumors), and/or prevention of postoperative recurrence thereof, as well as methods for inducing CTLs, methods for inducing an immune response against cancers (tumors) and also anti-tumor immunity, wherein a subject has HLA-A0206 antigen, such methods including the step of administering the peptides of SEQ ID NO: 1 or SEQ ID NO: 2, exosomes or the antigen-presenting cells presenting SEQ ID NO: 1 or SEQ ID NO: 2 or the pharmaceutical agents of the invention. In addition, the CTLs of the present invention also find use as vaccines against cancer. Examples of target cancers include, but are not limited to, renal cancer, bladder cancer, cervical cancer, cholangiocellular carcinoma, esophageal cancer, gastric cancer, NSCLC, osteosarcoma, pancreatic cancer and soft tissue tumor.

It is to be understood that both the foregoing summary of the invention and the following detailed description are of exemplified embodiments, and not restrictive of the invention or other alternate embodiments of the invention.

BRIEF DESCRIPTION OF DRAWINGS

Various aspects and applications of the present invention will become apparent to the skilled artisan upon consideration of the brief description of the figures and the detailed description of the present invention and its preferred embodiments which follows:

FIG. 8 depicts a line graph showing specific CTL activity against the target cells that express URLC10 and HLA-A*0206. COS7 cells transfected with the full length of URLC10 gene alone or with HLA-A*0206 gene alone were prepared as control. The CTL clone established with URLC10-A0206-10-211 (SEQ ID NO: 2) showed high specific CTL activity against COS7 cells transfected with both HIG2 and HLA-A0206 (black lozenge-mark). On the other hand, no significant specific CTL activity was detected against target cells expressing either HLA-A0206 (open triangular mark) or URLC10 (open circle). In the figures, "R" means Responder and "S" means Stimulator.

DESCRIPTION OF EMBODIMENTS

Figure 1:
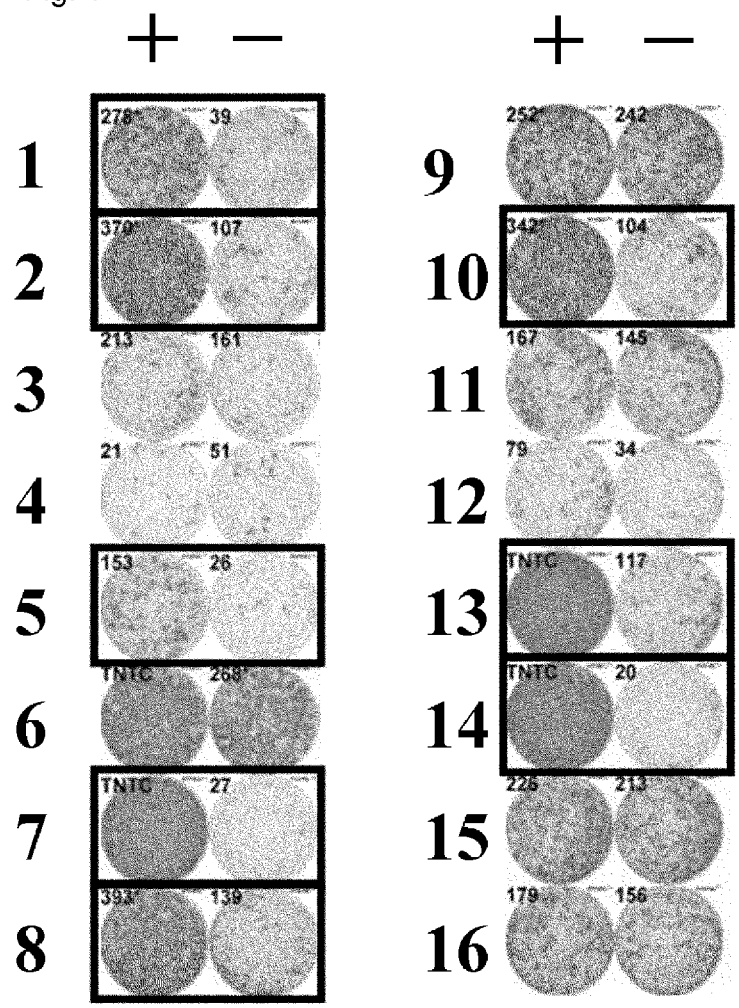
FIG. 1 includes a series of photographs depicting the results of IFN-gamma ELISPOT assay on CTLs that were induced with a peptide derived from HIG2. The CTLs in well #1, #2, #5, #7, #8, #10, #13 and #14 stimulated with HIG2-A0206-9-4 (SEQ ID NO: 1) showed potent IFN-gamma production as compared with the control. In the figures, "+" indicates that the target cells were pulsed with the appropriate peptide, and "−" indicates that the target cells were not been pulsed with any peptides.

Although any methods and materials similar or equivalent to those described herein can be used in the practice or testing of embodiments of the present invention, the preferred methods, devices, and materials are now described. However, before the present materials and methods are described, it is to be understood that the present invention is not limited to the particular sizes, shapes, dimensions, materials, methodologies, protocols, etc. described herein, as these may vary in accordance with routine experimentation and optimization. It is also to be understood that the terminology used in the description is for the purpose of describing the particular versions or embodiments only, and is not intended to limit the scope of the present invention which will be limited only by the appended claims.

The disclosure of each publication, patent or patent application mentioned in this specification is specifically incorporated by reference herein in its entirety. However, nothing herein is to be construed as an admission that the invention is not entitled to antedate such disclosure by virtue of prior invention.

In case of conflict, the present specification, including definitions, will control. In addition, the materials, methods, and examples are illustrative only and not intended to be limiting.

I. DEFINITIONS

The words "a", "an", and "the" as used herein mean "at least one" unless otherwise specifically indicated.

The terms "polypeptide", "peptide" and "protein" are used interchangeably herein to refer to a polymer of amino acid residues. The terms apply to amino acid polymers in which one or more amino acid residue is a modified residue, or a non-naturally occurring residue, such as an artificial chemical mimetic of a corresponding naturally occurring amino acid, as well as to naturally occurring amino acid polymers.

The term "amino acid" as used herein refers to naturally occurring and synthetic amino acids, as well as amino acid analogs and amino acid mimetics that similarly function to the naturally occurring amino acids. Naturally occurring amino acids are those encoded by the genetic code, as well as those modified after translation in cells (e.g., hydroxyproline, gamma-carboxyglutamate, and O-phosphoserine). The phrase "amino acid analog" refers to compounds that have the same basic chemical structure (an alpha carbon bound to a hydrogen, a carboxy group, an amino group, and an R group) as a naturally occurring amino acid but have a modified R group or modified backbones (e.g., homoserine, norleucine, methionine, sulfoxide, methionine methyl sulfonium). The phrase "amino acid mimetic" refers to chemical compounds that have different structures but similar functions to general amino acids.

Amino acids may be referred to herein by their commonly known three letter symbols or the one-letter symbols recommended by the IUPAC-IUB Biochemical Nomenclature Commission.

The terms "gene", "polynucleotides", "nucleotides" and "nucleic acids" are used interchangeably herein unless otherwise specifically indicated and are similarly to the amino acids referred to by their commonly accepted single-letter codes.

Unless otherwise defined, the terms "cancer" refers to cancers over-expressing the HIG2 or URLC10 gene. Examples of cancers over-expressing HIG2 include, but are not limited to, renal cancer and soft tissue carcinoma; examples of cancers over-expressing URLC10 gene include, but are not limited to, bladder cancer, cervical cancer, cholangiocellular carcinoma, esophageal cancer, gastric cancer, non-small cell lung cancer (NSCLC), osteosarcoma, pancreatic cancer and soft tissue tumor.

Unless otherwise defined, the terms "cytotoxic T lymphocyte", "cytotoxic T cell" and "CTL" are used interchangeably herein and, unless otherwise specifically indicated, refer to a sub-group of T lymphocytes that are capable of recognizing non-self cells (e.g., tumor cells, virus-infected cells) and inducing the death of such cells.

Unless otherwise defined, all technical and scientific terms used herein have the same meanings as commonly understood by one of ordinary skill in the art to which this invention belongs.

II. PEPTIDES

To demonstrate that peptides of HIG2-A0206-9-4 (SEQ ID NO: 1) and URLC10-A0206-10-211 (SEQ ID NO: 2) function as an antigen recognized by cytotoxic T lymphocytes (CTLs), these peptides were analyzed to determine whether they were antigen epitopes restricted by HLA-A0206. After in vitro stimulation of T-cells by dendritic cells (DCs) loaded with these peptides, CTLs were successfully established using each of the peptides of HIG2-A0206-9-4 (SEQ ID NO: 1) and URLC10-A0206-10-211 (SEQ ID NO: 2).

These established CTLs show potent specific CTL activity against target cells expressing HLA-A0206 antigen, which pulsed with respective peptides. The results herein demonstrate that the peptides may be epitope peptides of HIG2 and URLC10 restricted by HLA-A0206. Since these peptides may also be epitope peptides of HIG2 or URLC10 restricted by HLA-A0201 (WO2008/102557, PCT/JP2008/000290, incorporated by reference herein), pharmaceutical agent or composition comprising the peptides may be applicable to both HLA-A0201-positive subjects and HLA-A0206 positive subjects.

Since the HIG2 or URLC10 gene is over-expressed in most cancer tissues, such as bladder cancer, cervical cancer, cholangiocellular carcinoma, esophageal cancer, gastric cancer, NSCLC, osteosarcoma, pancreatic cancer, renal cancer and soft tissue tumor, it is a good target for immunotherapy. In particular, examples of cancer over-expressing HIG2 include renal cancer and soft tissue tumor. Also, examples of cancer over-expressing URLC10 include bladder cancer, cervical cancer, cholangiocellular carcinoma, esophageal cancer, gastric cancer, NSCLC, osteosarcoma, pancreatic cancer and soft tissue tumor. Thus, the present invention provides nonapeptides (peptides consisting of nine amino acid residues) and decapeptides (peptides consisting of ten amino acid residues) corresponding to epitope peptides of HIG2 or URLC10 restricted by HLA-A0206. Particularly preferred examples of nonapeptides and decapeptides of the present invention include those peptides having an amino acid sequence selected from among SEQ ID NOs: 1 and 2. More particularly, examples of epitope peptides of HIG2 restricted by HLA-A0206 includes the peptide comprising an amino acid sequence of SEQ ID NO: 1, and examples of epitope peptides of URLC10 restricted by HLA-A0206 include the peptide comprising an amino acid sequence of SEQ ID NO: 2.

In general, modification of one, two, or more amino acids in a protein will not influence the function of the protein, or in some cases even enhance the desired function of the original protein. In fact, modified peptides (i.e., peptides composed of an amino acid sequence in which one, two or several amino acid residues have been modified (i.e., substituted, deleted, added and/or inserted) as compared to an original reference sequence) have been known to retain the biological activity of the original peptide (Mark et al., Proc Natl Acad Sci USA 1984, 81: 5662-6; Zoller and Smith, Nucleic Acids Res 1982, 10: 6487-500; Dalbadie-McFarland et al., Proc Natl Acad Sci USA 1982, 79: 6409-13). Thus, in one embodiment, the peptides of the present invention may have both CTL inducibility and an amino acid sequence of SEQ ID NO: 1 or 2 wherein one, two or even more amino acids are added, inserted, deleted, and/or substituted.

Those of skill in the art recognize that individual additions or substitutions to an amino acid sequence which alters a single amino acid or a small percentage of amino acids tend to result in the conservation of the properties of the original amino acid side-chain. As such, they are conventionally referred to as "conservative substitutions" or "conservative modifications", wherein the alteration of a protein results in a modified protein having properties and functions analogous to the original protein. Conservative substitution tables providing functionally similar amino acids are well known in the art. Examples amino acid side chain characteristics that are desirable to conserve include, for example, hydrophobic amino acids (A, I, L, M, F, P, W, Y, V), hydrophilic amino acids (R, D, N, C, E, Q, G, H, K, S, T), and side chains having the following functional groups or characteristics in common: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic containing side-chain (H, F, Y, W). In addition, the following eight groups each contain amino acids that are accepted in the art as conservative substitutions for one another:

1) Alanine (A), Glycine (G);
2) Aspartic acid (D), Glutamic acid (E);
3) Aspargine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, Proteins 1984).

Such conservatively modified peptides are also considered to be peptides of the present invention. However, peptides of the present invention are not restricted thereto and can include non-conservative modifications, so long as the peptide retains the CTL inducibility of the original peptide. Furthermore, modified peptides should not exclude CTL inducible peptides of polymorphic variants, interspecies homologues, and alleles of HIG2 or URLC10.

When used in the context of immunotherapy, peptides of the present invention should be presented on the surface of a cell or exosome, preferably as a complex with an HLA-A0206 antigen. Therefore, it is preferable to select peptides that not only induce CTLs but also that possess high binding affinity to the HLA-A0206 antigen. To that end, the peptides can be modified by substitution, insertion, deletion, and/or addition of the amino acid residues to yield a modified peptide having improved binding affinity. In addition to peptides that are naturally displayed, since the regularity of the sequences of peptides displayed by binding to HLA antigens is already known (J Immunol 1994, 152: 3913; Immunogenetics 1995, 41: 178; J Immunol 1994, 155: 4307), modifications based on such regularity can be introduced into the immunogenic peptides of the invention. Substitutions can be introduced not only at the terminal amino acids but also at the position of potential TCR recognition of peptides. Several studies have demonstrated that amino acid substitutions in a peptide can be equal to or better than the original, for example CAP1, p53$_{(264-272)}$, Her-2/neu$_{(369-377)}$ or gp100$_{(209-217)}$ (Zaremba et al. Cancer Res. 57, 4570-4577, 1997, T. K. Hoffmann et al. J Immunol. (2002) Feb. 1; 168(3):1338-47, S. O. Dionne et al. Cancer Immunol immunother. (2003) 52: 199-206 and S. O. Dionne et al. Cancer Immunology, Immunotherapy (2004) 53, 307-314).

The present invention also contemplates the addition one to two amino acids can also be added to the N and/or C-terminus of the present peptides. Such modified peptides having high HLA antigen binding affinity and retained CTL inducibility are also included in the present invention.

However, when the peptide sequence is identical to a portion of the amino acid sequence of an endogenous or exogenous protein having a different function, side effects such as autoimmune disorders and/or allergic symptoms against specific substances may be induced. Therefore, it is preferable to first perform homology searches using available databases to avoid situations in which the sequence of the peptide matches the amino acid sequence of another protein. When it becomes clear from the homology searches that there exists not even a peptide with 1 or 2 amino acid differences as compared to the objective peptide, the objective peptide can be modified in order to increase its binding affinity with HLA antigens, and/or increase its CTL inducibility without any danger of such side effects.

Although peptides modified as described above are expected to be highly effective, the candidate peptides are examined for the presence of CTL inducibility to select higher effective peptides. Herein, the phrase "CTL inducibility" indicates the ability of the peptide to induce cytotoxic lymphocytes (CTLs) when presented on antigen-presenting cells. Further, "CTL inducibility" includes the ability of the peptide to induce CTL activation, CTL proliferation, promote CTL lysis of target cells, and to increase CTL IFN-gamma production.

Confirmation of CTL inducibility is accomplished by inducing antigen-presenting cells carrying human MHC antigens (for example, B-lymphocytes, macrophages, and dendritic cells (DCs)), or more specifically DCs derived from human peripheral blood mononuclear leukocytes, and after stimulation with the peptides, mixing with CD8-positive cells, and then measuring the IFN-gamma produced and released by CTL against the target cells. As the reaction system, transgenic animals that have been produced to express a human HLA-A0206 antigen can be used (BenMohamed L, Krishnan R, Longmate J, Auge C, Low L, Primus J, Diamond D J, Hum Immunol 2000 August, 61(8): 764-79). For example, the target cells can be radio-labeled with $^{51}$Cr and such, and cytotoxic activity can be calculated from radioactivity released from the target cells which HLA antigen is HLA-A0206. Alternatively, CTL inducibility can be assessed by measuring IFN-gamma produced and released by CTL in the presence of antigen-presenting cells (APCs) that carry immobilized peptides, and visualizing the inhibition zone on the media using anti-IFN-gamma monoclonal antibodies.

In addition to the above-described modifications, the peptides of the present invention can also be linked to other substances, so long as the resulting linked peptide retains the requisite CTL inducibility of the original peptide. Examples of suitable substances include, but are not limited to: peptides, lipids, sugar and sugar chains, acetyl groups, natural and synthetic polymers, etc. The peptides can contain modifications such as glycosylation, side chain oxidation, or phosphorylation, etc. provided the modifications do not destroy the biological activity of the original peptide. These kinds of modifications can be performed to confer additional functions (e.g., targeting function, and delivery function) or to stabilize the polypeptide.

For example, to increase the in vivo stability of a polypeptide, it is known in the art to introduce D-amino acids, amino acid mimetics or unnatural amino acids; this concept can also be adapted to the present polypeptides. The stability of a polypeptide can be assayed in a number of ways. For instance, peptidases and various biological media, such as human plasma and serum, can be used to test stability (see, e.g., Verhoef et al., Eur J Drug Metab Pharmacokin 1986, 11: 291-302).

Further, the peptides of the present invention may be linked to other peptides via spacers or linkers. Examples of other peptides include, but are not limited to, CTL inducible peptides derived from other TAAs. Alternatively, two or more peptides of the present invention may be linked via spacers or linkers. The peptides linked via spacers or linkers may be the same or different each other. Spacers or linkers are not specifically limited, but are preferably peptides, more preferably peptides having one or more cleavage sites which are capable of being cleaved by enzymes such as peptidases, proteases and proteasomes. Examples of linkers or spacers include, but are not limited to: AAY (P. M. Daftarian et al., J Trans Med 2007, 5:26), AAA, NKRK (R. P. M. Sutmuller et al., J Immunol. 2000, 165: 7308-7315) or, one to several lysine redsidues (S. Ota et al., Can Res. 62, 1471-1476, K. S. Kawamura et al., J Immunol. 2002, 168: 5709-5715). The peptide of the present invention encompass those peptides linked to other peptides via spacers or linkers.

The peptides of the present invention may be existed on the surface of a cell carrying human MHC antigens (e.g. antigen presenting cell) or an exosome as complexes in combination with MHC molecules and then induce CTLs. The cells and the exosomes can be prepared by well-known methods in the art, for example, the cells may be prepared by contacting with the peptides of the present invention, and the exosomes may be prepared by collecting an exosome-containing fraction from the cells contacted with the peptides of the present invention (see, e.g., Japanese Patent Application Kohyo Publications No. Hei 11-510507 and WO99/03499). The peptides of the present invention encompass those peptides existed on the surface of a cell or an exosome as complexes in combination with MHC molecules.

Herein, the peptides of the present invention can also be described as "HIG2 or URLC10 peptide(s)" or "HIG2 or URLC10 polypeptide(s)".

III. PREPARATION OF PEPTIDES

The peptides of the present invention can be prepared using well known techniques. For example, the peptides can be prepared synthetically, using recombinant DNA technology or chemical synthesis. The peptides of the present invention can be synthesized individually or as longer polypeptides composed of two or more peptides. The peptides can then be isolated i.e., purified or isolated so as to be substantially free of other naturally occurring host cell proteins and fragments thereof, or any other chemical substances.

A peptide of the present invention can be obtained through chemical synthesis based on the selected amino acid sequence. Examples of conventional peptide synthesis methods that can be adapted to the synthesis include, but are not limited to:

(i) Peptide Synthesis, Interscience, New York, 1966;
(ii) The Proteins, Vol. 2, Academic Press, New York, 1976;
(iii) Peptide Synthesis (in Japanese), Maruzen Co., 1975;
(iv) Basics and Experiment of Peptide Synthesis (in Japanese), Maruzen Co., 1985;
(v) Development of Pharmaceuticals (second volume) (in Japanese), Vol. 14 (peptide synthesis), Hirokawa, 1991;
(vi) WO99/67288; and
(vii) Barany G. & Merrifield R. B., Peptides Vol. 2, "Solid Phase Peptide Synthesis", Academic Press, New York, 1980, 100-118.

Alternatively, the present peptides can be obtained adapting any known genetic engineering methods for producing peptides (e.g., Morrison J, J Bacteriology 1977, 132: 349-51; Clark-Curtiss & Curtiss, Methods in Enzymology (eds. Wu et al.) 1983, 101: 347-62). For example, first, a suitable vector harboring a polynucleotide encoding the objective peptide in an expressible form (e.g., downstream of a regulatory sequence corresponding to a promoter sequence) is prepared and transformed into a suitable host cell. The host cell is then cultured to produce the peptide of interest. The peptide can also be produced in vitro adopting an in vitro translation system.

IV. POLYNUCLEOTIDES

The present invention also provides a polynucleotide which encodes the aforementioned peptides of the present invention. These include polynucleotides derived from the natural occurring HIG2 or URLC10 gene (SEQ ID NO: 3 or 5, GenBank Accession NO NM_013332 or NM_017527) as well as those having a conservatively modified nucleotide sequence thereof. Herein, the phrase "conservatively modified nucleotide sequence" refers to sequences which encode identical or essentially identical amino acid sequences. Due to the degeneracy of the genetic code, a large number of functionally identical nucleic acids encode any given protein. For instance, the codons GCA, GCC, GCG, and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a peptide also describes every possible silent variation of the nucleic acid. One of ordinary skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a peptide is implicitly described in each disclosed sequence.

The polynucleotide of the present invention can be composed of DNA, RNA, and derivatives thereof. A DNA is suitably composed of bases such as A, T, C, and G, and T is replaced by U in an RNA.

The polynucleotide of the present invention can encode multiple peptides of the present invention, with or without intervening amino acid sequences in between. For example, the intervening amino acid sequence can provide a cleavage site (e.g., enzyme recognition sequence) of the polynucleotide or the translated peptides. Furthermore, the polynucleotide can include any additional sequences to the coding sequence encoding the peptide of the present invention. For example, the polynucleotide can be a recombinant polynucleotide that includes regulatory sequences required for the expression of the peptide or can be an expression vector (plasmid) with marker genes and such. In general, such recombinant polynucleotides can be prepared by the manipulation of polynucleotides through conventional recombinant techniques using, for example, polymerases and endonucleases.

Both recombinant and chemical synthesis techniques can be used to produce the polynucleotides of the present invention. For example, a polynucleotide can be produced by insertion into an appropriate vector, which can be expressed when transfected into a competent cell. Alternatively, a polynucleotide can be amplified using PCR techniques or expression in suitable hosts (see, e.g., Sambrook et al., Molecular Cloning: A Laboratory Manual, Cold Spring Harbor Laboratory, New York, 1989). Alternatively, a polynucleotide can be synthesized using the solid phase techniques, as described in Beaucage S L & Iyer R P, Tetrahedron 1992, 48: 2223-311; Matthes et al., EMBO J 1984, 3: 801-5.

Vectors containing the polynucleotide of the present invention and host cells harboring the vectors are also included in the present invention.

V. EXOSOMES

The present invention further provides intracellular vesicles called exosomes, which present complexes formed between the peptides of this invention and HLA antigens on their surface. Exosomes can be prepared, for example, by using the methods detailed in Japanese Patent Application Kohyo Publications Nos. Hei 11-510507 and WO99/03499, and can be prepared using APCs obtained from patients who are subject to treatment and/or prevention. The exosomes of this invention can be inoculated as vaccines, in a fashion similar to the peptides of this invention.

In the context of the present invention, the type of HLA antigens included in the complexes should be HLA-A0206, and the subject to which the exosomes are inoculated must possess HLA-A0206 antigen. Typically, in the clinic, the type of HLA antigen of the patient requiring treatment is investigated in advance, which enables the appropriate selection of patients to be expected benefit for treatment with the exosomes of the present invention.

VI. ANTIGEN-PRESENTING CELLS (APCS)

The present invention also provides isolated APCs that present complexes formed between HLA-A0206 antigens and the peptides of this invention on its surface. The APCs that are obtained by contacting the peptides of this invention, or introducing the nucleotides encoding the peptides of this invention in an expressible form can be derived from patients who are subject to treatment and/or prevention, and can be administered as vaccines by themselves or in combination with other drugs including the peptides of this invention, exosomes, or cytotoxic T cells.

The APCs are not limited to a particular kind of cells and include dendritic cells (DCs), Langerhans cells, macrophages, B cells, and activated T cells, which are known to present proteinaceous antigens on their cell surface so as to be recognized by lymphocytes. Since DC is a representative APC having the strongest CTL inducing action among APCs, preferable APCs of the present invention are DCs.

For example, an APC can be obtained by inducing DCs from peripheral blood monocytes and then contacting (stimulating) them with the peptides of this invention in vitro, ex vivo or in vivo. When the peptides of this invention are administered to the subjects whose HLA-A antigen is HLA-A0206, APCs that present the peptides of this invention are induced in the body of the subject. The phrase "inducing APC" includes contacting (stimulating) a cell with the peptides of this invention, or nucleotides encoding the peptides of this invention to present complexes formed between HLA-A0206 antigens and the peptides of this invention on cell's surface. Alternatively, after introducing the peptides of this invention to the APCs to allow the APCs to present the peptides, the APCs can be administered to the subject as a vaccine. For example, the ex vivo administration can include the steps of:

a: collecting APCs from a first subject whose HLA-A antigen is HLA-A0206,
b: contacting with the APCs of step a, with the peptide and
c: administering the peptide-loaded APCs to a second subject whose HLA-A antigen is HLA-A0206.

The first subject and the second subject can be the same individual, or may be different individuals. Alternatively, according to the present invention, use of the peptides of this invention for manufacturing a pharmaceutical composition inducing antigen-presenting cells is provided. In addition, the present invention provides a method or process for manufacturing a pharmaceutical composition inducing antigen-presenting cells, wherein the method includes the step of admixing or formulating the peptide of the present invention with a pharmaceutically acceptable carrier. Further, the present invention also provides the peptides of the present invention for inducing antigen-presenting cells. The APCs obtained by step b can be administered to the subject as a vaccine.

According to an aspect of the present invention, the APCs have a high level of CTL inducibility. In the term of "high level of CTL inducibility", the high level is relative to the level of that by APC contacted with no peptide or peptides which can not induce the CTL. Such APCs having a high level of CTL inducibility can be prepared by a method which includes the step of transferring genes containing polynucleotides that encode the peptides of this invention to APCs in vitro. The introduced genes can be in the form of DNAs or RNAs. Examples of methods for introduction include, without particular limitations, various methods conventionally performed in this field, such as lipofection, electroporation, and calcium phosphate method can be used. More specifically, it can be performed as described in Cancer Res 1996, 56: 5672-7; J Immunol 1998, 161: 5607-13; J Exp Med 1996, 184: 465-72; Published Japanese Translation of International Publication No. 2000-509281. By transferring the gene into APCs, the gene undergoes transcription, translation, and such in the cell, and then the obtained protein is processed by MHC Class I or Class II, and proceeds through a presentation pathway to present peptides.

VII. CYTOTOXIC T CELLS (CTLS)

A cytotoxic T cell induced against any of the peptides of the present invention strengthens the immune response targeting tumor-associated endothelia in vivo and thus can be used as vaccines, in a fashion similar to the peptides per se. Thus, the present invention also provides isolated cytotoxic T cells that are specifically induced or activated by any of the present peptides.

Such cytotoxic T cells can be obtained by (1) administering the peptides of the present invention to a subject, and then collecting cytotoxic T cells from the subject or (2) contacting (stimulating) subject-derived APCs, and CD8-positive cells, or peripheral blood mononuclear leukocytes in vitro with the peptides of the present invention.

The cytotoxic T cells, which have been induced by stimulation from APCs that present the peptides of this invention, can be derived from patients who are subject to treatment and/or prevention and possess HLA-A0206 antigen, and can be administered by themselves or in combination with other drugs including the peptides of this invention or exosomes for the purpose of regulating effects. The obtained cytotoxic T cells act specifically against target cells presenting the peptides of this invention, or, for example, the same peptides used for induction. In the other word, the cytotoxic T cells can recognize (i.e., binding to) a complex formed between a HLA-A0206 and the peptide of the present invention on a target cell surface with the T cell receptor and then attack the target cell to induce the death of the target cell. The target cells can be cells that endogenously express HIG2 or URLC10, or cells that are transfected with the HIG2 or URLC10 gene; and cells that present a peptide of this invention on the cell surface due to stimulation by the peptide can also serve as targets of activated CTL attack.

VIII. T CELL RECEPTOR (TCR)

The present invention also provides a polynucleotide composed of a nucleic acid sequence encoding polypeptides that are capable of forming a subunit of a T cell receptor (TCR), and methods of using the same. The TCR subunits have the ability to form TCRs that confer specificity to T cells against tumor cells presenting HIG2 peptides or URLC10 peptides with an HLA-A0602 antigen. By using the known methods in the art, the nucleic acid sequence of alpha- and beta-chains of the TCR expressed in the CTL induced with the peptide of this invention can be identified (WO2007/032255 and Morgan et al., J Immunol, 171, 3288 (2003)). The derivative TCRs can bind to the HIG2 or URLC10 peptide displaying on the target cells with high avidity, and optionally mediate efficient killing of target cells presenting the HIG2 or URLC10 peptide with HLA-A0602 antigen in vivo and in vitro.

The nucleic acids sequence encoding the TCR subunits can be incorporated into suitable vectors, e.g., retroviral vectors. These vectors are well known in the art. The nucleic acids or the vectors containing them usefully can be transferred into a T cell, for example, a T cell from a patient whose HLA-A antigen is HLA-A0206. Advantageously, the present invention provides an off-the-shelf composition allowing rapid modification of a patient's own T cells (or those of another mammal) to rapidly and easily produce modified T cells having excellent cancer cell killing properties.

Also, the present invention provides CTLs which are prepared by transduction with a polynucleotide having the nucleic acid sequence encoding the TCR subunits polypeptides that bind to a complex formed between the HIG2 or URLC10 peptide and an HLA-A0206 antigen. The transduced CTLs are capable of homing to cancer cells in vivo, and can be expanded by well known culturing methods in vitro (e.g., Kawakami et al., J Immunol., 142, 3452-3461 (1989)). The T cells of the present invention can be used to form an immunogenic composition useful in treating or the prevention of cancer in a patient in need of therapy or protection (WO2006/031221).

IX. PHARMACEUTICAL AGENTS OR COMPOSITIONS

The terms "prevention" and "prophylaxis" are interchangeably used herein to refer to any activity that reduces the burden of mortality or morbidity from disease. Prevention and prophylaxis can occur "at primary, secondary and tertiary prevention levels." While primary prevention and prophylaxis avoid the development of a disease, secondary and tertiary levels of prevention and prophylaxis encompass activities aimed at the prevention and prophylaxis of the progression of a disease and the emergence of symptoms as well as reducing the negative impact of an already established disease by restoring function and reducing disease-related complications. Alternatively, prevention and prophylaxis can include a wide range of prophylactic therapies aimed at alleviating the severity of the particular disorder, e.g., reducing the proliferation and metastasis of tumors.

The treatment and/or prophylaxis of cancer and/or the prevention of postoperative recurrence thereof include any of the following steps, such as the surgical removal of cancer cells, the inhibition of the growth of cancerous cells, the involution or regression of a tumor, the induction of remission and suppression of occurrence of cancer, the tumor regression, and the reduction or inhibition of metastasis. Effectively treating and/or the prophylaxis of cancer decreases mortality and improves the prognosis of individuals having cancer, decreases the levels of tumor markers in the blood, and alleviates detectable symptoms accompanying cancer. For example, reduction or improvement of symptoms constitutes effectively treating and/or the prophylaxis include 10%, 20%, 30% or more reduction, or stable disease.

Since HIG2 or URLC10 expression is up-regulated in several cancers as compared with normal tissues, the peptides of this invention or polynucleotides encoding such peptides can be used for the treatment and/or for the prophylaxis of cancer, and/or prevention of postoperative recurrence thereof. Thus, the present invention provides a pharmaceutical agent or composition for treating and/or preventing cancer, and/or preventing the postoperative recurrence thereof, which includes one or more of the peptides of this invention, or polynucleotides encoding the peptides as an active ingredient. Alternatively, the present peptides can be expressed on the surface of any of the foregoing exosomes or cells, such as APCs for the use as pharmaceutical agents or compositions. In addition, the aforementioned cytotoxic T cells which target any of the peptides of the present invention can also be used as the active ingredient of the present pharmaceutical agents or compositions. In the context of the present invention, the phrase "targeting a peptide" refers to recognizing (i.e., binding to) a complex formed between an HLA-A0206 antigen and a peptide on a target cell surface with the T cell receptor, and then attacking the target cell to induce the death of the target cell.

In another embodiment, the present invention also provides the use of an active ingredient selected from among:
 (a) a peptide of the present invention,
 (b) a nucleic acid encoding such a peptide as disclosed herein in an expressible form,
 (c) an APC of the present invention, and
 (d) a cytotoxic T cells of the present invention
 in manufacturing a pharmaceutical composition or agent for treating cancer.

Alternatively, the present invention further provides an active ingredient selected from among:
 (a) a peptide of the present invention,
 (b) a nucleic acid encoding such a peptide as disclosed herein in an expressible form,
 (c) an APC of the present invention, and
 (d) a cytotoxic T cells of the present invention
 for use in treating cancer.

Alternatively, the present invention further provides a method or process for manufacturing a pharmaceutical composition or agent for treating cancer, wherein the method or process includes the step of formulating a pharmaceutically or physiologically acceptable carrier with an active ingredient selected from among:
 (a) a peptide of the present invention,
 (b) a nucleic acid encoding such a peptide as disclosed herein in an expressible form,
 (c) an APC of the present invention, and
 (d) a cytotoxic T cells of the present invention
 as active ingredients.

In another embodiment, the present invention also provides a method or process for manufacturing a pharmaceutical composition or agent for treating cancer, wherein the method or process includes the step of admixing an active ingredient with a pharmaceutically or physiologically acceptable carrier, wherein the active ingredient is selected from among:

(a) a peptide of the present invention, (b) a nucleic acid encoding such a peptide as disclosed herein in an expressible form, (c) an APC of the present invention, and (d) a cytotoxic T cells of the present invention.

Alternatively, the pharmaceutical composition or agent of the present invention may be used for either or both the prophylaxis of cancer and prevention of postoperative recurrence thereof.

The present pharmaceutical agents or compositions find use as a vaccine. In the context of the present invention, the phrase "vaccine" (also referred to as an "immunogenic composition") refers to a substance that has the function to induce anti-tumor immunity upon inoculation into animals.

The pharmaceutical agents or compositions of the present invention can be used to treat and/or prevent cancers, and/or prevention of postoperative recurrence thereof in subjects or patients including human and any other mammal including, but not limited to, mouse, rat, guinea-pig, rabbit, cat, dog, sheep, goat, pig, cattle, horse, monkey, baboon, and chimpanzee, particularly a commercially important animal or a domesticated animal.

According to the present invention, polypeptides having an amino acid sequence selected from among SEQ ID NOs: 1 and 2 have been found to be HLA-A0206 restricted epitope peptides, that can induce potent and specific immune response against target cells expressing HIG2 or URLC10, and HLA-A0206. Therefore, the present pharmaceutical agents or compositions which include any of these polypeptides with the amino acid sequence selected from among SEQ ID NOs: 1 and 2 are particularly suited for the administration to subjects whose HLA antigen is HLA-A0206. The same applies to pharmaceutical agents or compositions which include polynucleotides encoding any of these polypeptides.

Cancers to be treated by the pharmaceutical agents or compositions of the present invention are not limited and include all kinds of cancers wherein HIG2 or URLC10 is involved, including, for example, bladder cancer, cervical cancer, cholangiocellular carcinoma, esophageal cancer, gastric cancer, NSCLC, osteosarcoma, pancreatic cancer, renal carcinoma and soft tissue tumor. Particularly, the pharmaceutical agents or compositions targeting HIG2 are preferably applicable to renal carcinoma and soft tissue tumor, and the pharmaceutical agents or compositions targeting URLC10 are preferably applicable to bladder cancer, cervical cancer, cholangiocellular carcinoma, esophageal cancer, gastric cancer, NSCLC, osteosarcoma, pancreatic cancer and soft tissue tumor.

The present pharmaceutical agents or compositions can contain in addition to the aforementioned active ingredients, other peptides which have the ability to induce CTLs against cancerous cells, other polynucleotides encoding the other peptides, other cells that present the other peptides, or such. Herein, the other peptides that have the ability to induce CTLs against cancerous cells are exemplified by cancer specific antigens (e.g., identified TAAs), but are not limited thereto.

If needed, the pharmaceutical agents or compositions of the present invention can optionally include other therapeutic substances as an active ingredient, so long as the substance does not inhibit the antitumoral effect of the active ingredient, e.g., any of the present peptides. For example, formulations can include anti-inflammatory agents or compositions, pain killers, chemotherapeutics, and the like. In addition to including other therapeutic substances in the medicament itself, the medicaments of the present invention can also be administered sequentially or concurrently with the one or more other pharmacologic agents or compositions. The amounts of medicament and pharmacologic agent or composition depend, for example, on what type of pharmacologic agent(s) or composition(s) is/are used, the disease being treated, and the scheduling and routes of administration.

It should be understood that in addition to the ingredients particularly mentioned herein, the pharmaceutical agents or compositions of this invention can include other agents or compositions conventional in the art having regard to the type of formulation in question.

In one embodiment of the present invention, the present pharmaceutical agents or compositions can be included in articles of manufacture and kits containing materials useful for treating the pathological conditions of the disease to be treated, e.g., cancer. The article of manufacture can include a container of any of the present pharmaceutical agents or compositions with a label. Suitable containers include bottles, vials, and test tubes. The containers can be formed from a variety of materials, such as glass or plastic. The label on the container should indicate the agent or compositions are used for treating or prevention of one or more conditions of the disease. The label can also indicate directions for administration and so on.

In addition to the container described above, a kit including a pharmaceutical agent or compositions of the present invention can optionally further include a second container housing a pharmaceutically-acceptable diluent. It can further include other materials desirable from a commercial and user standpoint, including other buffers, diluents, filters, needles, syringes, and package inserts with instructions for use.

The pharmaceutical compositions can, if desired, be presented in a pack or dispenser device which can contain one or more unit dosage forms containing the active ingredient. The pack can, for example, include metal or plastic foil, such as a blister pack. The pack or dispenser device can be accompanied by instructions for administration.

(1) Pharmaceutical Agents or Compositions Containing the Peptides as the Active Ingredient The peptides of this invention can be administered directly as a pharmaceutical agent or composition or, if necessary, that has been formulated by conventional formulation methods. In the latter case, in addition to the peptides of this invention, carriers, excipients, and such that are ordinarily used for drugs can be included as appropriate without particular limitations. Examples of such carriers are sterilized water, physiological saline, phosphate buffer, culture fluid and such. Furthermore, the pharmaceutical agents or compositions can contain as necessary, stabilizers, suspensions, preservatives, surfactants and such. The pharmaceutical agents or compositions of this invention can be used for anticancer purposes.

The peptides of this invention can be prepared as a combination composed of two or more of peptides of the invention, to induce CTL in vivo. The peptide combination can take the form of a cocktail or can be conjugated to each other using standard techniques. For example, the peptides can be chemically linked or expressed as a single fusion polypeptide sequence. The peptides in the combination can be the same or different. By administering the peptides of this invention, the peptides are presented at a high density by the HLA-A0206 antigen on APCs, then CTLs that specifically react toward the complex formed between the displayed peptide and the HLA-A0206 antigen are induced. Alternatively, APCs that present any of the peptides of this invention on their cell surface, which may be obtained by stimulating APCs (e.g., DCs) derived from the subjects whose HLA-A antigen is HLA-A0206 with the peptides of the present invention, may be administered to the subject, and as a result, CTLs are induced in the subject, and, aggressiveness towards the cancer cells, such as bladder cancer, cervical cancer, cholangiocellular carcinoma, esophageal cancer, gastric cancer, NSCLC, osteosarcoma, pancreatic cancer, renal carcinoma and soft tissue tumor can be increased.

The pharmaceutical agents or compositions for the treatment and/or prevention of cancer, which include a peptide of this invention as the active ingredient, can also include an adjuvant known to effectively establish cellular immunity. Alternatively, they can be administered with other active ingredients, and they can be administered by formulation into granules. An adjuvant refers to a compound that enhances the immune response against the protein when administered together (or successively) with the protein having immunological activity. Adjuvants contemplated herein include those described in the literature (Clin Microbiol Rev 1994, 7: 277-89). Examples of suitable adjuvants include, but are not limited to, aluminum phosphate, aluminum hydroxide, alum, cholera toxin, salmonella toxin, and such, but are not limited thereto.

Furthermore, liposome formulations, granular formulations in which the peptide is bound to few-micrometers diameter beads, and formulations in which a lipid is bound to the peptide may be conveniently used.

In some embodiments, the pharmaceutical agents or compositions of the present invention may further include a component which primes CTL. Lipids have been identified as agents or compositions capable of priming CTL in vivo against viral antigens. For example, palmitic acid residues can be attached to the epsilon- and alpha-amino groups of a lysine residue and then linked to a peptide of the invention. The lipidated peptide can then be administered either directly in a micelle or particle, incorporated into a liposome, or emulsified in an adjuvant. As another example of lipid priming of CTL responses, *E. coli* lipoproteins, such as tripalmitoyl-S-glycerylcysteinlyseryl-serine (P3CSS) can be used to prime CTL when covalently attached to an appropriate peptide (see, e.g., Deres et al., Nature 1989, 342: 561-4).

The method of administration can be oral, intradermal, subcutaneous, intravenous injection, or such, and systemic administration or local administration to the vicinity of the targeted sites. The administration can be performed by single administration or boosted by multiple administrations. The dose of the peptides of this invention can be adjusted appropriately according to the disease to be treated, age of the patient, weight, method of administration, and such, and is ordinarily 0.001 mg to 1000 mg, for example, 0.001 mg to 1000 mg, for example, 0.1 mg to 10 mg, and can be administered once in a few days to few months. One skilled in the art can appropriately select a suitable dose.

(2) Pharmaceutical Agents or Compositions Containing Polynucleotides as the Active Ingredient The pharmaceutical agents or compositions of the present invention can also contain nucleic acids encoding the peptides disclosed herein in an expressible form. Herein, the phrase "in an expressible form" means that the polynucleotide, when introduced into a cell, will be expressed in vivo as a polypeptide that induces anti-tumor immunity. In an exemplified embodiment, the nucleic acid sequence of the polynucleotide of interest includes regulatory elements necessary for expression of the polynucleotide. The polynucleotide(s) can be equipped so to achieve stable insertion into the genome of the target cell (see, e.g., Thomas K R & Capecchi M R, Cell 1987, 51: 503-12 for a description of homologous recombination cassette vectors). See, e.g., Wolff et al., Science 1990, 247: 1465-8; U.S. Pat. Nos. 5,580,859; 5,589,466; 5,804,566; 5,739,118; 5,736,524; 5,679,647; and WO 98/04720. Examples of DNA-based delivery technologies include "naked DNA", facilitated (bupivacaine, polymers, peptide-mediated) delivery, cationic lipid complexes, and particle-mediated ("gene gun") or pressure-mediated delivery (see, e.g., U.S. Pat. No. 5,922,687).

The peptides of the present invention can also be expressed by viral or bacterial vectors. Examples of expression vectors include attenuated viral hosts, such as vaccinia or fowlpox. This approach involves the use of vaccinia virus, e.g., as a vector to express nucleotide sequences that encode the peptide. Upon introduction into a host, the recombinant vaccinia virus expresses the immunogenic peptide, and thereby elicits an immune response. Vaccinia vectors and methods useful in immunization protocols are described in, e.g., U.S. Pat. No. 4,722,848. Examples of another vector include BCG (Bacille Calmette Guerin). BCG vectors are described in Stover et al., Nature 1991, 351: 456-60. A wide variety of other vectors useful for therapeutic administration or immunization, e.g., adeno and adeno-associated virus vectors, retroviral vectors, Salmonella typhi vectors, detoxified anthrax toxin vectors, and the like, will be apparent. See, e.g., Shata et al., Mol Med Today 2000, 6: 66-71; Shedlock et al., J Leukoc Biol 2000, 68: 793-806; Hipp et al., In Vivo 2000, 14: 571-85.

Delivery of a polynucleotide into a subject can be either direct, in which case the subject is directly exposed to a polynucleotide-carrying vector, or indirect, in which case, cells are first transformed with the polynucleotide of interest in vitro, then the cells are transplanted into the subject. Theses two approaches are known, respectively, as in vivo and ex vivo gene therapies.

For general reviews of the methods of gene therapy, see Goldspiel et al., Clinical Pharmacy 1993, 12: 488-505; Wu and Wu, Biotherapy 1991, 3: 87-95; Tolstoshev, Ann Rev Pharmacol Toxicol 1993, 33: 573-96; Mulligan, Science 1993, 260: 926-32; Morgan & Anderson, Ann Rev Biochem 1993, 62: 191-217; Trends in Biotechnology 1993, 11(5): 155-215). Methods commonly known in the art of recombinant DNA technology which can also be used for the present invention are described in eds. Ausubel et al., Current Protocols in Molecular Biology, John Wiley & Sons, NY, 1993; and Krieger, Gene Transfer and Expression, A Laboratory Manual, Stockton Press, NY, 1990.

The method of administration can be oral, intradermal, subcutaneous, intravenous injection, or such, and systemic administration or local administration to the vicinity of the targeted sites finds use. The administration can be performed by single administration or boosted by multiple administrations. The dose of the polynucleotide in the suitable carrier or cells transformed with the polynucleotide encoding the peptides of this invention can be adjusted appropriately according to the disease to be treated, age of the patient, weight, method of administration, and such, and is ordinarily 0.001 mg to 1000 mg, for example, 0.001 mg to 1000 mg, for example, 0.1 mg to 10 mg, and can be administered once every a few days to once every few months. One skilled in the art can appropriately select the suitable dose.

X. METHODS USING THE PEPTIDES, EXOSOMES, APCS AND CTLS

The peptides of the present invention and polynucleotides encoding such peptides can be used for inducing APCs and CTLs. The exosomes and APCs of the present invention can be also used for inducing CTLs. The peptides, polynucleotides, exosomes and APCs can be used in combination with any other compounds so long as the compounds do not inhibit their CTL inducibility. Thus, any of the aforementioned pharmaceutical agents or compositions of the present invention can be used for inducing CTLs, and in addition thereto, those including the peptides and polynucleotides can also be used for inducing APCs as discussed below.

(1) Method of Inducing Antigen-Presenting Cells (APCs)

The present invention provides methods of inducing APCs using the peptides of this invention or polynucleotides encoding the peptides. The induction of APCs can be performed as described above in section "VI. Antigen-presenting cells". This invention also provides a method for inducing APCs having a high level of CTL inducibility, the induction of which has been also mentioned under the item of "VI. Antigen-presenting cells", supra.

Preferably, the methods for inducing APCs include at least one step selected from among:

a: contacting APCs whose HLA-A antigen is HLA-A0206 with the peptides of the present invention, and b: introducing the polypeptides of the present invention in an expressible form into APCs whoses HLA-A antigen is HLA A0206.

Such methods for inducing APCs are preferably performed in vitro or ex vivo. When the methods performed in vitro or ex vivo, APCs to be induced may be obtained from a subject to be treated or others whose HLA-A antigen is HLA-A0206.

(2) Method of Inducing CTLs

Furthermore, the present invention provides methods for inducing CTLs using the peptides of this invention, polynucleotides encoding the peptides, or exosomes or APCs presenting the peptides.

The present invention also provides methods for inducing CTLs using a polynucleotide encoding a polypeptide that is capable of forming a T cell receptor (TCR) subunit recognizing (i.e., binding to) a complex of the peptides of the present invention and an HLA-A0206 antigen on a cell surface Preferably, the methods for inducing CTLs include at least one step selected from among:

a: contacting a CD8-positive T cell with an antigen-presenting cell and/or an exosome that presents on its surface a complex of an HLA-A0206 antigen and a peptide of the present invention, and b: introducing a polynucleotide encoding a polypeptide that is capable of forming a TCR subunit recognizing a complex of a peptide of the present invention and an HLA-A0206 antigen into a CD8 positive T cell.

When the peptides of this invention are administered to a subject, CTL is induced in the body of the subject, and the strength of the immune response targeting the cancer cells is enhanced. Alternatively, the peptides and polynucleotides encoding the peptides can be used for an ex vivo therapeutic method, in which subject-derived APCs, and CD8-positive cells, or peripheral blood mononuclear leukocytes are contacted (stimulated) with the peptides of this invention in vitro, and after inducing CTL, the activated CTL cells are returned to the subject. For example, the method can include steps of:

a: collecting APCs from subject whose HLA-A antigen is HLA-A0206:

b: contacting with the APCs of step a, with the peptide of the present invention:

c: mixing the APCs of step b with $CD^{8+}$ T cells whose HLA-A antigen is HLA-A0206, and co-culturing for inducing CTLs: and d: collecting $CD^{8+}$ T cells from the co-culture of step c.

Alternatively, according to the present invention, use of the peptides of this invention for manufacturing a pharmaceutical composition inducing CTLs is provided. In addition, the present invention provides a method or process for manufacturing a pharmaceutical agent or composition inducing CTLs, wherein the method includes the step of admixing or formulating the peptide of the present invention with a pharmaceutically acceptable carrier. Further, the present invention also provides the peptide of the present invention for inducing CTLs.

The $CD^{8+}$ T cells having cytotoxic activity obtained by step d can be administered to the subject as a vaccine. The APCs to be mixed with the $CD^{8+}$ T cells in above step c can also be prepared by transferring genes coding for the present peptides into the APCs as detailed above in section "VI. Antigen-presenting cells"; but are not limited thereto and any APC or exosome which effectively presents the present peptides to the T cells can be used for the present method.

The following examples are presented to illustrate the present invention and to assist one of ordinary skill in making and using the same. The examples are not intended in any way to otherwise limit the scope of the invention.

EXAMPLES

Materials and Methods

Cell Lines

PSCCA0922 (HLA-A0206) was purchased from Pharma SNP Consortium; PSC. Human B-lymphoblastoid cell line, and COST were purchased from ATCC.

Candidate Peptides Derived from HIG2 and URLC10

9-mer and 10-mer peptides derived from HIG2 or URLC10 were synthesized by Sigma (Sapporo, Japan) or Biosynthesis Inc. (Lewisville, Tex.) according to a standard solid phase synthesis method and purified by reversed phase high performance liquid chromatography (HPLC). The purity (>90%) and the identity of the peptides were determined by analytical HPLC and mass spectrometry analysis, respectively. Peptides were dissolved in dimethylsulfoxide (DMSO) at 20 mg/ml and stored at −80 degrees C.

In Vitro CTL Induction

Monocyte-derived dendritic cells (DCs) were used as antigen-presenting cells (APCs) to induce cytotoxic T lymphocyte (CTL) responses against peptides presented on human leukocyte antigen (HLA). DCs were generated in vitro as described elsewhere (Nakahara S et al., Cancer Res 2003 Jul. 15, 63(14): 4112-8). Specifically, peripheral blood mononuclear cells (PBMCs) isolated from a normal volunteer (HLA-A0206 positive) by Ficoll-Plaque (Pharmacia) solution were separated by adherence to a plastic tissue culture dish (Becton Dickinson) so as to enrich them as the monocyte fraction. The monocyte-enriched population was cultured in the presence of 1000 U/ml of granulocyte-macrophage colony-stimulating factor (GM-CSF) (R&D System) and 1000 U/ml of interleukin (IL)-4 (R&D System) in AIM-V Medium (Invitrogen) containing 2% heat-inactivated autologous serum (AS). After 7 days of culture, the cytokine-induced DCs were pulsed with 20 micro-g/ml of each of the synthesized peptides in the presence of 3 micro-g/ml of beta2-microglobulin for 3 hrs at 37 degrees C. in AIM-V Medium. The generated cells appeared to express DC-associated molecules, such as CD80, CD83, CD86 and HLA class II, on their cell surfaces (data not shown). These peptide-pulsed DCs were then inactivated by Mitomycin C (MMC) (30 micro-g/ml for 30 min) and mixed at a 1:20 ratio with autologous CD8+ T cells, obtained by positive selection with CD8 Positive Isolation Kit (Dynal). These cultures were set up in 48-well plates (Corning); each well contained 1.5×10$^4$ peptide-pulsed DCs, 3×10$^5$ CD8+ T cells and 10 ng/ml of IL-7 (R&D System) in 0.5 ml of AIM-V/2% AS medium. Three days later, these cultures were supplemented with IL-2 (CHIRON) to a final concentration of 20 IU/ml. On day 7 and 14, the T cells were further stimulated with the autologous peptide-pulsed DCs. The DCs were prepared each time by the same way described above. CTL was tested against peptide-pulsed PSCCA0922 cells after the 3rd round of peptide stimulation on day 21 (Tanaka H et al., Br J Cancer 2001 Jan. 5, 84(1): 94-9; Umano Y et al., Br J Cancer 2001 Apr. 20, 84(8): 1052-7; Uchida N et al., Clin Cancer Res 2004 Dec. 15, 10(24): 8577-86; Suda T et al., Cancer Sci 2006 May, 97(5): 411-9; Watanabe T et al., Cancer Sci 2005 August, 96(8): 498-506).

CTL Expansion Procedure

CTLs were expanded in culture using the method similar to the one described by Riddell et al. (Walter E A et al., N Engl J Med 1995 Oct. 19, 333(16): 1038-44; Riddell S R et al., Nat Med 1996 February, 2(2): 216-23). A total of 5×10$^4$ CTLs were suspended in 25 ml of AIM-V/5% AS medium with 2 kinds of human B-lymphoblastoid cell lines, inactivated by MMC, in the presence of 40 ng/ml of anti-CD3 monoclonal antibody (Pharmingen). One day after initiating the cultures, 120 IU/ml of IL-2 were added to the cultures. The cultures were fed with fresh AIM-V/5% AS medium containing 30 IU/ml of IL-2 on days 5, 8 and 11 (Tanaka H et al., Br J Cancer 2001 Jan. 5, 84(1): 94-9; Umano Y et al., Br J Cancer 2001 Apr. 20, 84(8): 1052-7; Uchida N et al., Clin Cancer Res 2004 Dec. 15, 10(24): 8577-86; Suda T et al., Cancer Sci 2006 May, 97(5): 411-9; Watanabe T et al., Cancer Sci 2005 August, 96(8): 498-506).

Establishment of CTL Clones

The dilutions were made to have 0.3, 1, and 3 CTLs/well in 96 round-bottomed micro titer plate (Nalge Nunc International). CTLs were cultured with 7×10$^4$ cells/well of 2 kinds of human B-lymphoblastoid cell lines, 30 ng/ml of anti-CD3 antibody, and 125 U/ml of IL-2 in total of 150 micro l/well of AIM-V containing 5% AS. 50 micro l/well of IL-2 was added to the medium 10 days later so that IL-2 became 125 U/ml in the final concentration. CTL activity of CTLs was tested on the 14th day, and CTL clones were expanded using the same method above.

Specific CTL Activity

To examine specific CTL activity, interferon (IFN)-gamma enzyme-linked immunospot (ELISPOT) assay and IFN-gamma enzyme-linked immunosorbent assay (ELISA) were performed. Specifically, peptide-pulsed PSCCA0922 (1×10$^4$/well) was prepared as stimulator cells. Cultured cells in 48 wells were used as responder cells. IFN-gamma ELISPOT assay and IFN-gamma ELISA assay were performed under manufacture procedure.

Establishment of the Cells Forcibly Expressing Either or Both of the Target Gene and the HLA-A0206 Gene The cDNA encoding an open reading frame of target genes (HIG2; SEQ ID NO: 3 and URLC10; SEQ ID NO: 5) or HLA-A0206 (SEQ ID NO: 7) was amplified by PCR. The PCR-amplified product was cloned into pcDNA3.1 myc-His vector (Invitrogen). The plasmids contained either or both of the target genes and HLA-A0206 were transfected into COS7 using lipofectamine (Invitrogen) according to the manufacturer's recommended procedures. Briefly, 2.5×10$^6$ COS7 cells were pulsed with 10 micro-g plasmid at 140V and 1000 micro F. After 2 days from transfection, the transfected cells were treated with Cell dissociation solution and used as the target cells for CTL activity assay.

Results

Enhanced HIG2 and URLC10 Expression in Cancers

The global gene expression profile data obtained from various cancers using cDNA-microarray revealed that HIG2 (GenBank Accession No. NM_013332; SEQ ID No: 3) and URLC10 (GenBank Accession No. NM_017527; SEQ ID No: 5) expression was elevated. HIG2 expression was validly elevated in 19 out of 20 renal cancer and 7 out of 9 soft tissue tumor in comparing with corresponding normal tissues. URLC10 expression was validly elevated in 29 out of 29 bladder cancer, 15 out of 16 cervical cancer, 7 out of 7 cholangiocellular carcinoma, 7 out of 19 esophageal cancer, 3 out of 3 gastric cancer, 24 out of 27 NSCLC, 15 out of 19 osteosarcoma, 4 out of 5 pancreatic cancer and 33 out of 43 soft tissue tumor in comparing with corresponding normal tissues.

Figure 2:
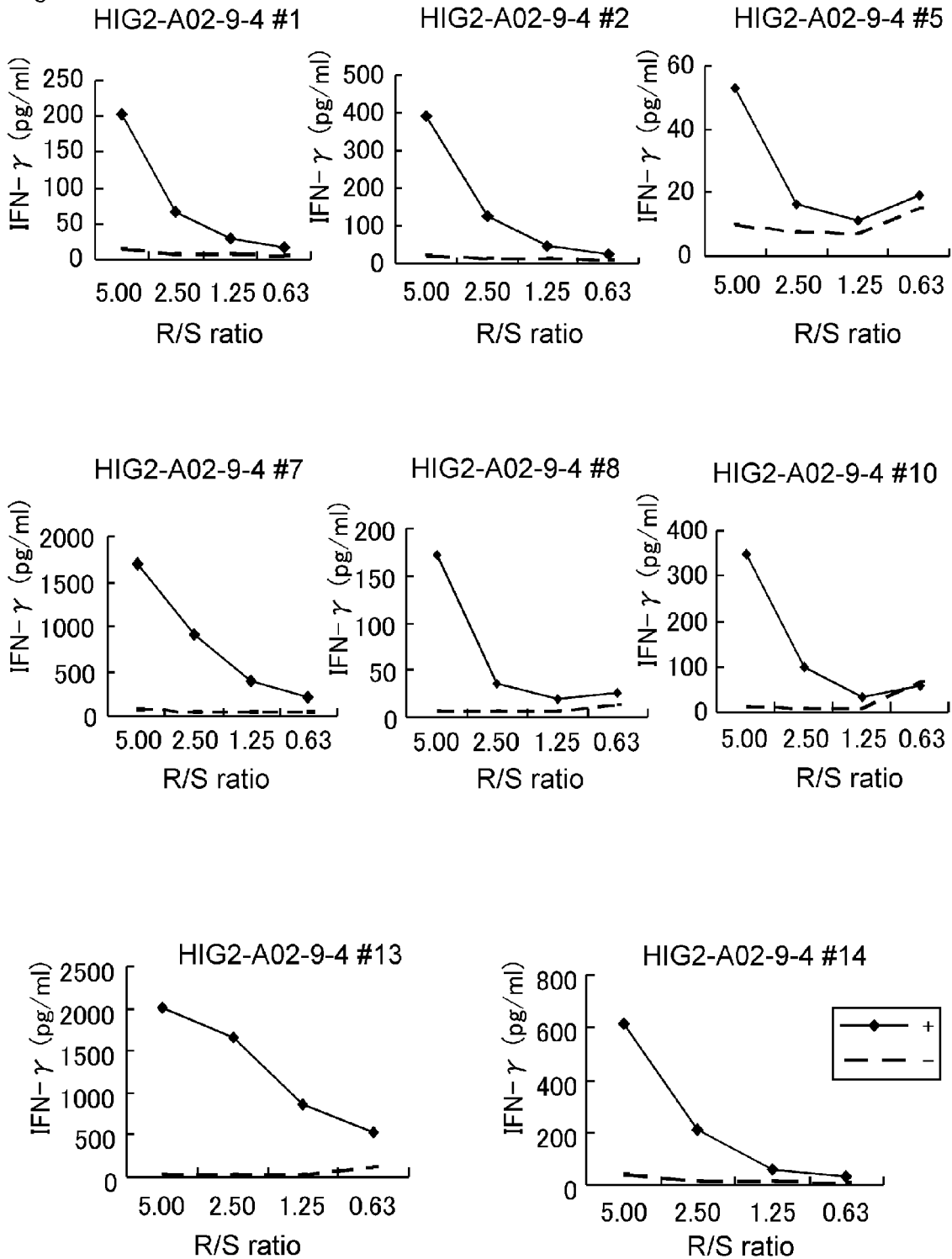
FIG. 2 depicts a series of line graphs showing the results of establishment of CTL lines stimulated with HIG2-A0206-9-4 (SEQ ID NO: 1) with IFN-gamma ELISA assay. It demonstrated that CTL lines established by stimulation with HIG2-A0206-9-4 (SEQ ID NO: 1) showed potent IFN-gamma production as compared with the control. In the figures, "+" indicates that the target cells were pulsed with the appropriate peptide, and "−" indicates that the target cells had not been pulsed with any peptides.

CTL Induction with the Peptide from HIG2 Restricted with HLA-A0206 and Establishment for CTL Lines Stimulated with HIG2 Derived Peptides CTLs for the peptide derived from HIG2 were generated according to the protocols as described in "Materials and Methods". Peptide specific CTL activity was determined by IFN-gamma ELISPOT assay (FIG. 1). The results herein show that HIG2-A0206-9-4 (SEQ ID NO: 1) demonstrates potent IFN-gamma production as compared to the control wells. Furthermore, the cells in the positive well numbers 1, 2, 5, 7, 8, 10, 13 and 14 stimulated with SEQ ID NO: 1 were expanded to establish CTL lines. CTL activities of those CTL lines were determined by IFN-gamma ELISA assay (FIG. 2). The results herein show that all CTL lines demonstrate potent IFN-gamma production against the target cells pulsed with corresponding peptide as compared to target cells without peptide pulse. Thus, HIG2-A0206-9-4 can induce potent CTL lines against the target cells which express HLA-A0206.

Establishment for CTL Clones Stimulated with HIG2 Derived Peptides

Figure 3:
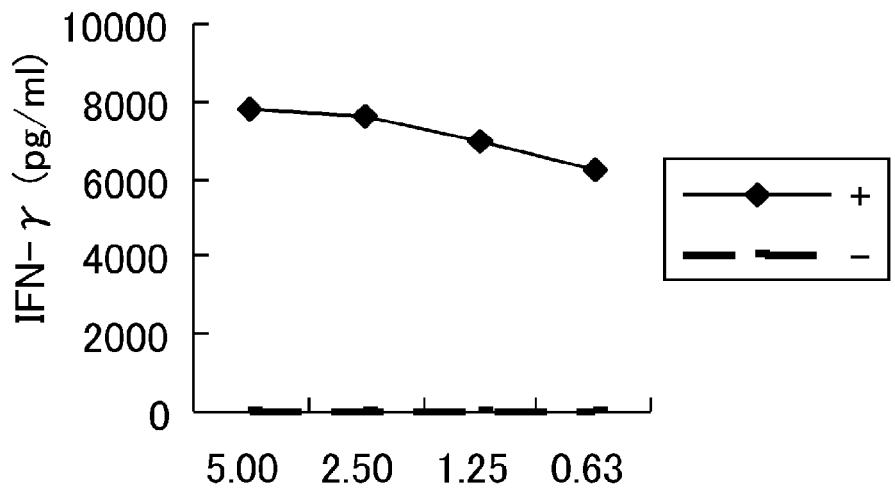
FIG. 3 depicts a line graph showing the results of the establishment of a CTL clone stimulated with HIG2-A0206-9-4 (SEQ ID NO: 1) with IFN-gamma ELISA assay. The results demonstrate that the CTL clone established by stimulation with HIG2-A0206-9-4 (SEQ ID NO: 1) showed potent IFN-gamma production as compared with the control. In the figures, "+" indicates that the target cells were pulsed with the appropriate peptide, and "−" indicates that the target cells had not been pulsed with any peptides.

The limiting dilution from these CTL lines was performed according to the protocols set forth in the "Materials and Methods" section above. The establishment of a CTL clone from HIG2-A0206-9-4 (SEQ ID NO: 1) CTL line is shown in FIG. 3. These CTL clones had potent and specific CTL activities against the peptide-pulsed target as compared to the activities against target without peptide pulse.

Specific CTL Activity Against the Target Cells Expressing HIG2 and HLA-A0206

Figure 4:
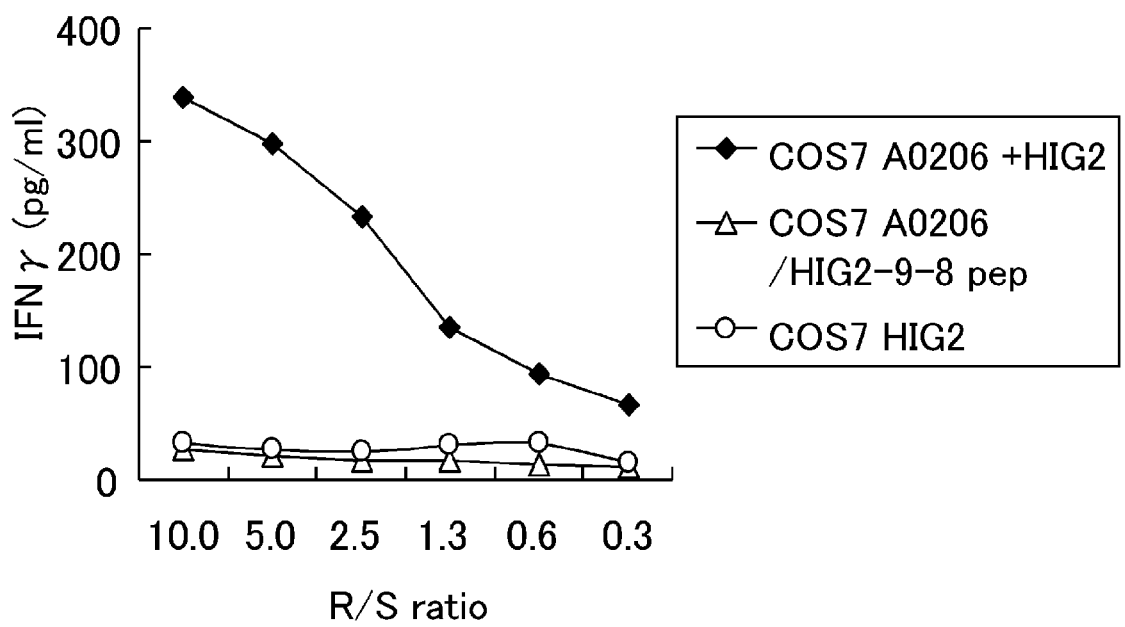
FIG. 4 depicts a line graph showing the specific CTL activity against the target cells that express HIG2 and HLA-A*0206. COS7 cells transfected with HLA-A*0206 alone and pulsed with an inappropriate peptide derived from HIG2, or with HIG2 alone were prepared as control. The CTL clone established with HIG2-A0206-9-4 (SEQ ID NO: 1) showed high specific CTL activity against COS7 cells transfected with both HIG2 and HLA-A0206 (black lozenge-mark). On the other hand, no significant specific CTL activity was detected against target cells expressing either HLA-A0206 (open triangular mark) or HIG2 (open circle).

The established CTL clones raised against HIG2-A0206-9-4 (SEQ ID NO: 1) were examined for their ability to recognize the target cells expressing HIG2 and HLA-A0206. Specific CTL activity against COS7 transfected with both full length HIG2 gene and the HLA-A0206 molecule, which serves as a specific model for the target cells endogenously express HIG2 and HLA-A0206, was tested using as effector cells the CTL clone raised by HIG2-A0206-9-4 (SEQ ID NO: 1). COS7 transfected with HLA-A0206 but not full length HIG2 and pulsed with other peptide (HIG2-9-8:YLLGVV-LTL) and COS7 transfected with full length HIG2 but not HLA-A0206 were prepared as controls. The CTL clones demonstrating the highest specific CTL activity against COS7 were those transfected with both HIG2 and HLA-A0206 (FIG. 4).

The results herein clearly demonstrate that HIG2-A0206-9-4 (SEQ ID NO: 1) is naturally processed and presented on the target cell surface with HLA-A0206 molecule and recognize CTL. Therefore, HIG2-A0206-9-4 may serve as a cancer vaccine targeting HIG2 expressed cancer cells in a subject whose HLA antigen is HLA-A0206.

Figure 5:
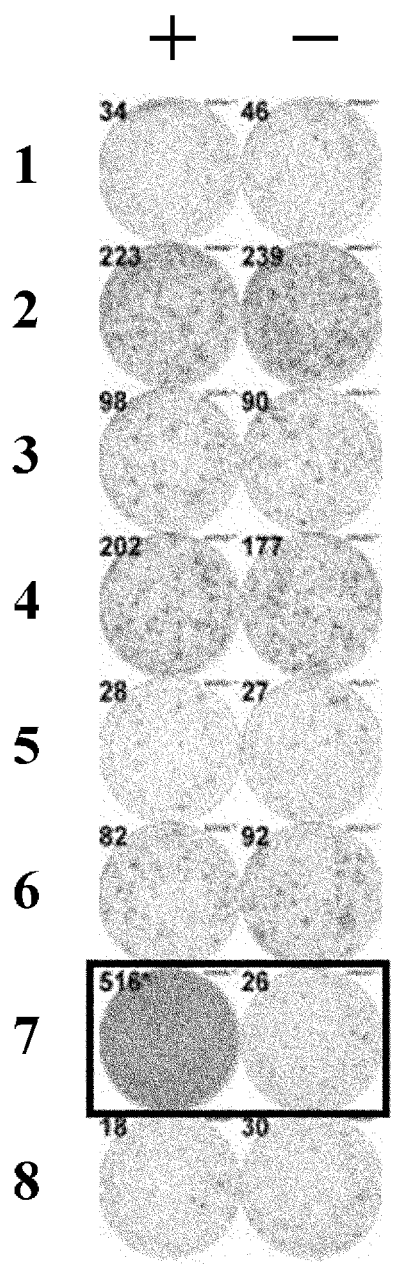
FIG. 5 includes a series of photographs depicting the results of IFN-gamma ELISPOT assay on CTLs that were induced with a peptide derived from URLC10. The CTLs in the well #7 stimulated with URLC10-A0206-10-211 (SEQ ID NO: 2) showed potent IFN-gamma production compared with the control. In the figures, "+" indicates that the target cells were pulsed with the appropriate peptide, and "−" indicates that the target cells had not been pulsed with any peptides.
Figure 6:
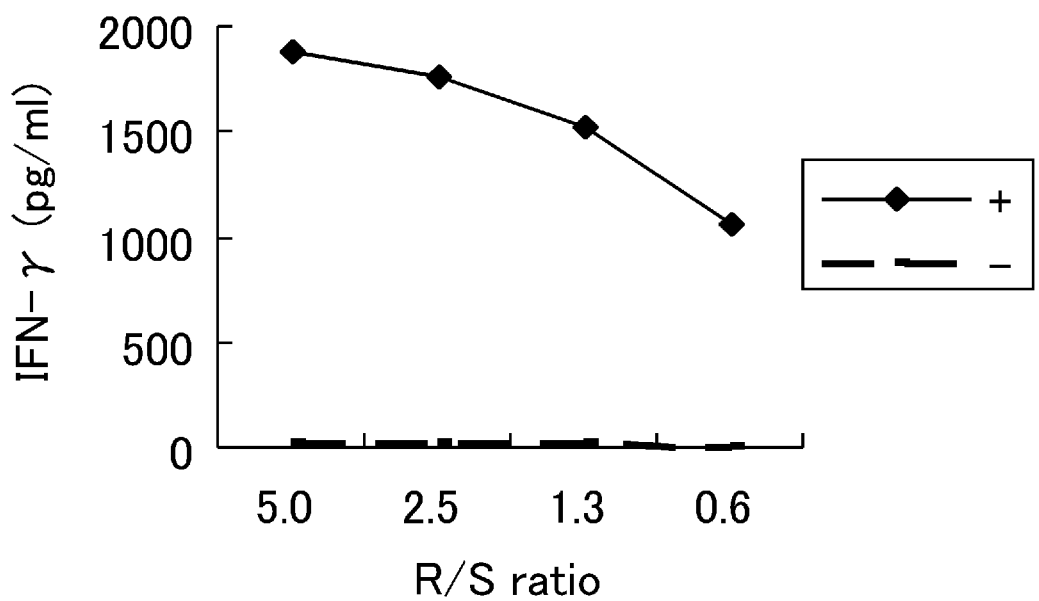
FIG. 6 depicts a line graph showing the results of the establishment of CTL lines stimulated with URLC10-A0206-10-211 (SEQ ID NO: 2) with IFN-gamma ELISA assay. The results demonstrate that CTL line established by stimulation with URLC10-A0206-10-211 (SEQ ID NO: 2) showed potent IFN-gamma production compared with the control. In the figures, "+" indicates that the target cells were pulsed with the appropriate peptide, and "−" indicates that the target cells had not been pulsed with any peptides.

CTL Induction with the Peptide from URLC10 Restricted with HLA-A0206 and Establishment for CTL Lines Stimulated with URLC10 Derived Peptides CTLs for the peptides derived from URLC10 were generated according to the protocols as described in "Materials and Methods". Peptide specific CTL activity was determined by IFN-gamma ELISPOT assay (FIG. 5). The results herein show that URLC10-A0206-10-211 (SEQ ID NO: 2) demonstrates potent IFN-gamma production as compared to the control wells. Furthermore, the cells in the positive well number 7 stimulated with SEQ ID NO: 2 were expanded and established CTL line. CTL activity of the CTL line was determined by IFN-gamma ELISA assay (FIG. 6). The result herein show that CTL line demonstrates potent IFN-gamma production against the target cells pulsed with corresponding peptide as compared to target cells without peptide pulse. Thus, URLC10-A0206-10-211 can induce potent CTL line.

Establishment for CTL Clone Stimulated with URLC10 Derived Peptide

Figure 7:
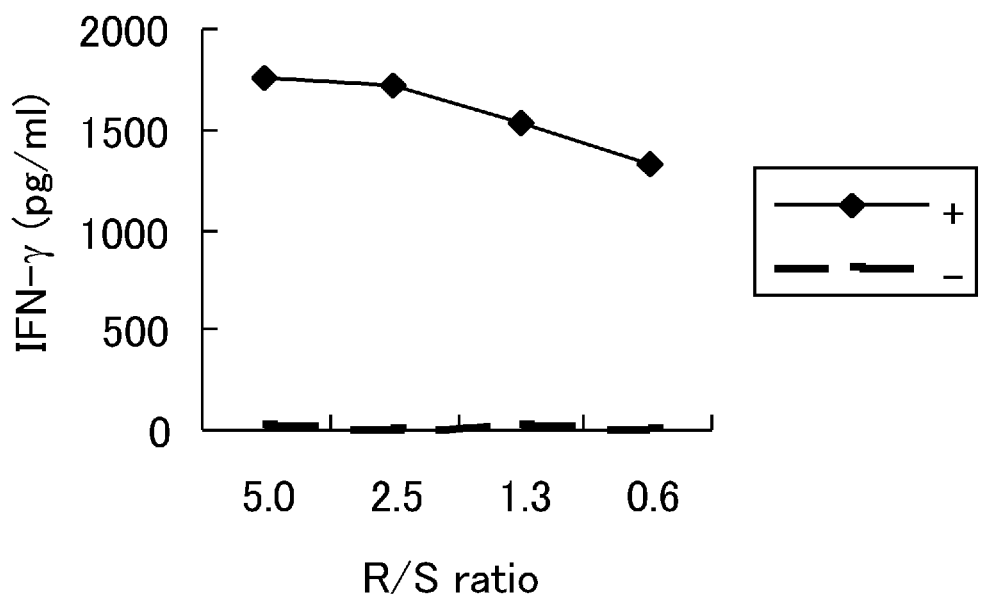
FIG. 7 depicts a line graph showing the result of the establishment of CTL clone stimulated with URLC10-A0206-10-211 (SEQ ID NO: 2) with IFN-gamma ELISA assay. The results demonstrate that CTL clone established by stimulation with URLC10-A0206-10-211 (SEQ ID NO: 2) showed potent IFN-gamma production compared with the control. In the figures, "+" indicates that the target cells were pulsed with the appropriate peptide, and "−" indicates that the target cells had not been pulsed with any peptides.

The limiting dilution from these CTL line was performed according to the protocols set forth in the "Materials and Methods" section above. The establishment of CTL clone from URLC10-A0206-10-211 (SEQ ID NO: 2) CTL line is shown in FIG. 7. This CTL clone has potent and specific CTL activity against the peptide-pulsed target as compared to the activities against target without peptide pulse.

Specific CTL Activity Against the Target Cells Expressing URLC10 and HLA-A0206

The established CTL clones raised against URLC10-A0206-10-211 (SEQ ID NO: 2) were examined for their ability to recognize the target cells expressing URLC10 and HLA-A0206. Specific CTL activity against COS7 transfected with both full length URLC10 gene and the HLA-A0206 molecule, which serves as a specific model for the target cells endogenously express URLC10 and HLA-A0206, was tested using as effector cells the CTL clone raised by URLC10-A0206-10-211 (SEQ ID NO: 2). COS7 transfected with full length URLC10 but not HLA-A0206 and COS7 transfected with HLA-A0206 but not full length URLC10 were prepared as controls. The CTL clone demonstrating the highest specific CTL activity against COS7 was that transfected with both URLC10 and HLA-A0206 (FIG. 8).

The results herein clearly demonstrate that URLC10-A0206-10-211 SEQ ID NO: 2) is naturally processed and presented on the target cell surface with HLA-A0206 molecule and recognize CTL. Furthermore, URLC10-A0206-10-211 may serve as a cancer vaccine targeting URLC10 expressed cancer cells in a subject whose HLA antigen is HLA-A0206.

In conclusion, novel HLA-A0206 epitope peptides HIG2-A0206-9-4 (SEQ ID NO: 1) and URLC10-A0206-10-211 (SEQ ID NO: 2) were identified and demonstrate as applicable for cancer immunotherapy in a subject whose HLA-A antigen is HLA-A0206.

INDUSTRIAL APPLICABILITY

The present invention describes new TAAs, particularly those derived from HIG2 or URLC10 that induce potent and specific anti-tumor immune responses and have applicability to a wide array of cancer types. Such TAAs warrant further development as peptide vaccines against diseases associated with HIG2 or URLC10, e.g., cancers such as bladder cancer, cervical cancer, cholangiocellular carcinoma, esophagus cancer, gastric cancer, non-small cell lung cancer (NSCLC), osteosarcoma, pancreatic cancer, renal carcinoma and soft tissue tumor.

While the invention is herein described in detail and with reference to specific embodiments thereof, it is to be understood that the foregoing description is exemplary and explanatory in nature and is intended to illustrate the invention and its preferred embodiments. Through routine experimentation, one skilled in the art will readily recognize that various changes and modifications can be made therein without departing from the spirit and scope of the invention, the metes and bounds of which are defined by the appended claims.

The invention claimed is:

1. A method for inducing an antigen-presenting cell with high CTL inducibility, wherein the method comprises the steps of
   a) collecting APCs from a subject whose HLA-A antigen is HLA-A0206, and
   b) contacting the APCs of step a with a peptide consisting of an amino acid sequence selected from the group consisting of SEQ ID NO: 1 and 2.

2. A method for inducing a CTL comprising the steps of:
   a) collecting APCs from a subject whose HLA-A antigen is HLA-A0206,
   b) contacting the APCs of step a with a peptide consisting of an amino acid sequence selected from the group consisting of SEQ ID NO: 1 and 2,
   c) mixing the APCs of step b with CD8+ T cells whose HLA-A antigen is HLA-A0206, and co-culturing for inducing CTLs, and
   d) collecting CD8+ T cells from the co-culture of step c.

3. A method of inducing immune response against cancer in a subject whose HLA antigen is HLA-A0206, wherein said method comprises the step of administering to said subject an agent comprising:

(a) 0.1 mg to 10 mg of a peptide consisting of an amino acid sequence selected from the group consisting of SEQ ID NO: 1 and 2;
   (b) a polynucleotide encoding the peptide of (a);
   (c) an isolated antigen-presenting cell that presents on its surface a complex of an HLA-A0206 antigen and a peptide consisting of an amino acid sequence selected from the group consisting of SEQ ID NO: 1 and 2; or
   (d) an isolated CTL which recognizes a complex of an HLA-A0206 antigen and a peptide consisting of an amino acid sequence selected from the group consisting of SEQ ID NO: 1 and 2, wherein the agent is administered with subcutaneous injection along with adjuvant.

4. The method of claim 3, wherein said cancer is selected from the group consisting of bladder cancer, cervical cancer, cholangiocellular carcinoma, esophagus cancer, gastric cancer, NSCLC, osteosarcoma, pancreatic cancer, renal carcinoma and soft tissue tumor.

* * * * *

SEQUENCE LISTING

```
<160> NUMBER OF SEQ ID NOS: 8

<210> SEQ ID NO 1
<211> LENGTH: 9
<212> TYPE: PRT
<213> ORGANISM: Artificial
<220> FEATURE:
<223> OTHER INFORMATION: An artificially synthesized peptide

<400> SEQUENCE: 1

Val Leu Asn Leu Tyr Leu Leu Gly Val
1               5

<210> SEQ ID NO 2
<211> LENGTH: 10
<212> TYPE: PRT
<213> ORGANISM: Artificial
<220> FEATURE:
<223> OTHER INFORMATION: An artificially synthesized peptide

<400> SEQUENCE: 2

Leu Leu Leu Ala Ser Ile Ala Ala Gly Leu
1               5                   10

<210> SEQ ID NO 3
```

<211> LENGTH: 1372
<212> TYPE: DNA
<213> ORGANISM: Homo sapiens
<220> FEATURE:
<221> NAME/KEY: CDS
<222> LOCATION: (206)..(397)

<400> SEQUENCE: 3

```
gcacgagggc gcttttgtct ccggtgagtt ttgtggcggg aagcttctgc gctggtgctt      60
agtaaccgac tttcctccgg actcctgcac gacctgctcc tacagccggc gatccactcc     120
cggctgttcc cccggagggt ccagaggcct ttcagaagga aaggcagct ctgtttctct      180 gcagaggagt agggtccttt cagcc atg aag cat gtg ttg aac ctc tac ctg       232
                              Met Lys His Val Leu Asn Leu Tyr Leu
                                1               5 tta ggt gtg gta ctg acc cta ctc tcc atc ttc gtt aga gtg atg gag       280
Leu Gly Val Val Leu Thr Leu Leu Ser Ile Phe Val Arg Val Met Glu
 10              15                  20                  25 tcc cta gaa ggc tta cta gag agc cca tcg cct ggg acc tcc tgg acc       328
Ser Leu Glu Gly Leu Leu Glu Ser Pro Ser Pro Gly Thr Ser Trp Thr
                 30                  35                  40 acc aga agc caa cta gcc aac aca gag ccc acc aag ggc ctt cca gac       376
Thr Arg Ser Gln Leu Ala Asn Thr Glu Pro Thr Lys Gly Leu Pro Asp
             45                  50                  55 cat cca tcc aga agc atg tga taagacctcc ttccatactg gccatatttt         427
His Pro Ser Arg Ser Met
             60 ggaacactga cctagacatg tccagatggg agtcccattc ctagcagaca agctgagcac     487 cgttgtaacc agagaactat tactaggcct tgaagaacct gtctaactgg atgctcattg     547 cctgggcaag gcctgtttag gccggttgcg gtggctcatg cctgtaatcc tagcactttg     607 ggaggctgag gtgggtggat cacctgaggt caggagttcg agaccagcct cgccaacatg     667 gcgaaacccc atctctacta aaaatacaaa agttagctgg gtgtggtggc agaggcctgt     727 aatcccagtt ccttgggagg ctgaggcggg agaattgctt gaacccgggg acggaggttg     787 cagtgaaccg agatcgcact gctgtaccca gcctgggcca cagtgcaaga ctccatctca     847 aaaaaaaaaa gaaaagaaaa agcctgttta atgcacaggt gtgagtggat tgcttatggc     907 tatgagatag gttgatctcg cccttacccc ggggtctggt gtatgctgtg ctttcctcag     967 cagtatggct ctgacatctc ttagatgtcc aacttcagc tgttgggaga tggtgatatt    1027 ttcaaccta cttcctaaac atctgtctgg ggttccttta gtcttgaatg tcttatgctc    1087 aattatttgg tgttgagcct ctcttccaca agagctcctc catgtttgga tagcagttga    1147 agaggttgtg tgggtgggct gttgggagtg aggatggagt gttcagtgcc catttctcat    1207 tttacattt aaagtcgttc ctccaacata gtgtgtattg gtctgaaggg ggtggtggga    1267 tgccaaagcc tgctcaagtt atggacattg tggccaccat gtggcttaaa tgatttttc    1327 taactaataa agtggaatat atatttcaaa aaaaaaaaa aaaaa                    1372
```

<210> SEQ ID NO 4
<211> LENGTH: 63
<212> TYPE: PRT
<213> ORGANISM: Homo sapiens

<400> SEQUENCE: 4

```
Met Lys His Val Leu Asn Leu Tyr Leu Leu Gly Val Val Leu Thr Leu
 1               5                  10                  15

Leu Ser Ile Phe Val Arg Val Met Glu Ser Leu Glu Gly Leu Leu Glu
```

```
                              20                  25                  30
Ser Pro Ser Pro Gly Thr Ser Trp Thr Thr Arg Ser Gln Leu Ala Asn
             35                  40                  45

Thr Glu Pro Thr Lys Gly Leu Pro Asp His Pro Ser Arg Ser Met
     50                  55                  60

<210> SEQ ID NO 5
<211> LENGTH: 1735
<212> TYPE: DNA
<213> ORGANISM: Homo sapiens
<220> FEATURE:
<221> NAME/KEY: CDS
<222> LOCATION: (242)..(913)

<400> SEQUENCE: 5
gttatcagag gtgagcccgt gctcttcagc ggagaagatc ccctacctgg ccgccggcca      60
ctttctgtgg gccgtggggt cctcaaggag acggcccttg ggctcagggg ctgcgtttcc     120
acacgcgcct ttcccagggc tcccgcgccc gttcctgcct ggccgccggc cgctccaaca     180
gcagcacaag gcgggactca gaaccggcgt tcagggccgc cagcggccgc gaggccctga     240 g atg agg ctc caa aga ccc cga cag gcc ccg gcg ggt ggg agg cgc gcg     289
  Met Arg Leu Gln Arg Pro Arg Gln Ala Pro Ala Gly Gly Arg Arg Ala
  1               5                  10                  15 ccc cgg ggc ggg cgg ggc tcc ccc tac cgg cca gac ccg gga aga ggc       337
Pro Arg Gly Gly Arg Gly Ser Pro Tyr Arg Pro Asp Pro Gly Arg Gly
             20                  25                  30 gcg cgg agg ctg cga agg ttc cag aag ggc ggg gag ggg gcg ccg cgc       385
Ala Arg Arg Leu Arg Arg Phe Gln Lys Gly Gly Glu Gly Ala Pro Arg
         35                  40                  45 gct gac cct ccc tgg gca ccg ctg ggg acg atg gcg ctg ctc gcc ttg       433
Ala Asp Pro Pro Trp Ala Pro Leu Gly Thr Met Ala Leu Leu Ala Leu
     50                  55                  60 ctg ctg gtc gtg gcc cta ccg cgg gtg tgg aca gac gcc aac ctg act       481
Leu Leu Val Val Ala Leu Pro Arg Val Trp Thr Asp Ala Asn Leu Thr
65                  70                  75                  80 gcg aga caa cga gat cca gag gac tcc cag cga acg gac gag ggt gac       529
Ala Arg Gln Arg Asp Pro Glu Asp Ser Gln Arg Thr Asp Glu Gly Asp
                 85                  90                  95 aat aga gtg tgg tgt cat gtt tgt gag aga gaa aac act ttc gag tgc       577
Asn Arg Val Trp Cys His Val Cys Glu Arg Glu Asn Thr Phe Glu Cys
             100                 105                 110 cag aac cca agg agg tgc aaa tgg aca gag cca tac tgc gtt ata gcg       625
Gln Asn Pro Arg Arg Cys Lys Trp Thr Glu Pro Tyr Cys Val Ile Ala
         115                 120                 125 gcc gtg aaa ata ttt cca cgt ttt ttc atg gtt gcg aag cag tgc tcc       673
Ala Val Lys Ile Phe Pro Arg Phe Phe Met Val Ala Lys Gln Cys Ser
     130                 135                 140 gct ggt tgt gca gcg atg gag aga ccc aag cca gag gag aag cgg ttt       721
Ala Gly Cys Ala Ala Met Glu Arg Pro Lys Pro Glu Glu Lys Arg Phe
145                 150                 155                 160 ctc ctg gaa gag ccc atg ccc ttc ttt tac ctc aag tgt tgt aaa att       769
Leu Leu Glu Glu Pro Met Pro Phe Phe Tyr Leu Lys Cys Cys Lys Ile
                 165                 170                 175 cgc tac tgc aat tta gag ggg cca cct atc aac tca tca gtg ttc aaa       817
Arg Tyr Cys Asn Leu Glu Gly Pro Pro Ile Asn Ser Ser Val Phe Lys
             180                 185                 190 gaa tat gct ggg agc atg ggt gag agc tgt ggt ggg ctg tgg ctg gcc       865
Glu Tyr Ala Gly Ser Met Gly Glu Ser Cys Gly Gly Leu Trp Leu Ala
         195                 200                 205
```

```
atc ctc ctg ctg ctg gcc tcc att gca gcc ggc ctc agc ctg tct tga      913
Ile Leu Leu Leu Leu Ala Ser Ile Ala Ala Gly Leu Ser Leu Ser
    210                 215                 220 gccacgggac tgccacagac tgagccttcc ggagcatgga ctcgctccag accgttgtca     973
cctgttgcat taaacttgtt ttctgttgat tacctcttgg tttgacttcc cagggtcttg    1033
ggatgggaga gtggggatca ggtgcagttg gctcttaacc ctcaagggtt ctttaactca    1093
cattcagagg aagtccagat ctcctgagta gtgattttgg tgacaagttt ttctctttga    1153
aatcaaacct tgtaactcat ttattgctga tggccactct tttccttgac tcccctctgc    1213
ctctgagggc ttcagtattg atggggaggg aggcctaagt accactcatg gagagtatgt    1273
gctgagatgc ttccgacctt tcaggtgacg caggaacact gggggagtct gaatgattgg    1333
ggtgaagaca tccctggagt gaaggactcc tcagcatggg gggcagtggg gcacacgtta    1393
gggctgcccc cattccagtg gtggaggcgc tgtggatggc tgcttttcct caacctttcc    1453
taccagattc caggaggcag aagataacta attgtgttga agaaacttag acttcaccca    1513
ccagctggca caggtgcaca gattcataaa ttcccacacg tgtgtgttca acatctgaaa    1573
cttaggccaa gtagagagca tcagggtaaa tggcgttcat ttctctgtta agatgcagcc    1633
atccatgggg agctgagaaa tcagactcaa agttccacca aaaacaaata caaggggact    1693
tcaaaagttc acgaaaaaat tgaattaaaa gataaaaatt aa                       1735

<210> SEQ ID NO 6
<211> LENGTH: 223
<212> TYPE: PRT
<213> ORGANISM: Homo sapiens

<400> SEQUENCE: 6

Met Arg Leu Gln Arg Pro Arg Gln Ala Pro Ala Gly Gly Arg Arg Ala
1               5                   10                  15

Pro Arg Gly Gly Arg Gly Ser Pro Tyr Arg Pro Asp Pro Gly Arg Gly
            20                  25                  30

Ala Arg Arg Leu Arg Arg Phe Gln Lys Gly Gly Glu Gly Ala Pro Arg
        35                  40                  45

Ala Asp Pro Pro Trp Ala Pro Leu Gly Thr Met Ala Leu Leu Ala Leu
    50                  55                  60

Leu Leu Val Val Ala Leu Pro Arg Val Trp Thr Asp Ala Asn Leu Thr
65                  70                  75                  80

Ala Arg Gln Arg Asp Pro Glu Asp Ser Gln Arg Thr Asp Glu Gly Asp
                85                  90                  95

Asn Arg Val Trp Cys His Val Cys Glu Arg Glu Asn Thr Phe Glu Cys
            100                 105                 110

Gln Asn Pro Arg Arg Cys Lys Trp Thr Glu Pro Tyr Cys Val Ile Ala
        115                 120                 125

Ala Val Lys Ile Phe Pro Arg Phe Phe Met Val Ala Lys Gln Cys Ser
    130                 135                 140

Ala Gly Cys Ala Ala Met Glu Arg Pro Lys Pro Glu Glu Lys Arg Phe
145                 150                 155                 160

Leu Leu Glu Glu Pro Met Pro Phe Phe Tyr Leu Lys Cys Cys Lys Ile
                165                 170                 175

Arg Tyr Cys Asn Leu Glu Gly Pro Pro Ile Asn Ser Ser Val Phe Lys
            180                 185                 190

Glu Tyr Ala Gly Ser Met Gly Glu Ser Cys Gly Gly Leu Trp Leu Ala
        195                 200                 205
```

```
Ile Leu Leu Leu Ala Ser Ile Ala Ala Gly Leu Ser Leu Ser
    210             215             220
```

```
<210> SEQ ID NO 7
<211> LENGTH: 1098
<212> TYPE: DNA
<213> ORGANISM: Homo sapiens
<220> FEATURE:
<221> NAME/KEY: CDS
<222> LOCATION: (1)..(1098)

<400> SEQUENCE: 7
```

```
atg gcc gtc atg gcg ccc cga acc ctc gtc ctg cta ctc tcg ggg gct    48
Met Ala Val Met Ala Pro Arg Thr Leu Val Leu Leu Leu Ser Gly Ala
1               5                   10                  15 ctg gcc ctg acc cag acc tgg gcg ggc tct cac tcc atg agg tat ttc    96
Leu Ala Leu Thr Gln Thr Trp Ala Gly Ser His Ser Met Arg Tyr Phe
                20                  25                  30 tac acc tcc gtg tcc cgg ccc ggc cgc ggg gag ccc cgc ttc atc gca   144
Tyr Thr Ser Val Ser Arg Pro Gly Arg Gly Glu Pro Arg Phe Ile Ala
            35                  40                  45 gtg ggc tac gtg gac gac acg cag ttc gtg cgg ttc gac agc gac gcc   192
Val Gly Tyr Val Asp Asp Thr Gln Phe Val Arg Phe Asp Ser Asp Ala
        50                  55                  60 gcg agc cag agg atg gag ccg cgg gcg ccg tgg ata gag cag gag ggt   240
Ala Ser Gln Arg Met Glu Pro Arg Ala Pro Trp Ile Glu Gln Glu Gly
65                  70                  75                  80 ccg gag tat tgg gac ggg gag aca cgg aaa gtg aag gcc cac tca cag   288
Pro Glu Tyr Trp Asp Gly Glu Thr Arg Lys Val Lys Ala His Ser Gln
                85                  90                  95 act cac cga gtg gac ctg ggg acc ctg cgc ggc tac tac aac cag agc   336
Thr His Arg Val Asp Leu Gly Thr Leu Arg Gly Tyr Tyr Asn Gln Ser
                100                 105                 110 gag gcc ggt tct cac acc gtc cag agg atg tat ggc tgc gac gtg ggg   384
Glu Ala Gly Ser His Thr Val Gln Arg Met Tyr Gly Cys Asp Val Gly
            115                 120                 125 tcg gac tgg cgc ttc ctc cgc ggg tac cac cag tac gcc tac gac ggc   432
Ser Asp Trp Arg Phe Leu Arg Gly Tyr His Gln Tyr Ala Tyr Asp Gly
        130                 135                 140 aag gat tac atc gcc ctg aaa gag gac ctg cgc tct tgg acc gcg gcg   480
Lys Asp Tyr Ile Ala Leu Lys Glu Asp Leu Arg Ser Trp Thr Ala Ala
145                 150                 155                 160 gac atg gca gct cag acc acc aag cac aag tgg gag gcg gcc cat gtg   528
Asp Met Ala Ala Gln Thr Thr Lys His Lys Trp Glu Ala Ala His Val
                165                 170                 175 gcg gag cag ttg aga gcc tac ctg gag ggc acg tgc gtg gag tgg ctc   576
Ala Glu Gln Leu Arg Ala Tyr Leu Glu Gly Thr Cys Val Glu Trp Leu
                180                 185                 190 cgc aga tac ctg gag aac ggg aag gag acg ctg cag cgc acg gac gcc   624
Arg Arg Tyr Leu Glu Asn Gly Lys Glu Thr Leu Gln Arg Thr Asp Ala
            195                 200                 205 ccc aaa acg cat atg act cac cac gct gtc tct gac cat gaa gcc acc   672
Pro Lys Thr His Met Thr His His Ala Val Ser Asp His Glu Ala Thr
        210                 215                 220 ctg agg tgc tgg gcc ctg agc ttc tac cct gcg gag atc aca ctg acc   720
Leu Arg Cys Trp Ala Leu Ser Phe Tyr Pro Ala Glu Ile Thr Leu Thr
225                 230                 235                 240 tgg cag cgg gat ggg gag gac cag acc cag gac acg gag ctc gtg gag   768
Trp Gln Arg Asp Gly Glu Asp Gln Thr Gln Asp Thr Glu Leu Val Glu
                245                 250                 255 acc agg cct gca ggg gat gga acc ttc cag aag tgg gcg gct gtg gtg   816
```

```
            Thr Arg Pro Ala Gly Asp Gly Thr Phe Gln Lys Trp Ala Ala Val Val
                    260                 265                 270 gtg cct tct gga cag gag cag aga tac acc tgc cat gtg cag cat gag        864
Val Pro Ser Gly Gln Glu Gln Arg Tyr Thr Cys His Val Gln His Glu
            275                 280                 285 ggt ttg ccc aag ccc ctc acc ctg aga tgg gag ccg tct tcc cag ccc        912
Gly Leu Pro Lys Pro Leu Thr Leu Arg Trp Glu Pro Ser Ser Gln Pro
        290                 295                 300 acc atc ccc atc gtg ggc atc att gct ggc ctg gtt ctc ttt gga gct        960
Thr Ile Pro Ile Val Gly Ile Ile Ala Gly Leu Val Leu Phe Gly Ala
305                 310                 315                 320 gtg atc act gga gct gtg gtc gct gct gtg atg tgg agg agg aag agc       1008
Val Ile Thr Gly Ala Val Val Ala Ala Val Met Trp Arg Arg Lys Ser
                325                 330                 335 tca gat aga aaa gga ggg agc tac tct cag gct gca agc agt gac agt       1056
Ser Asp Arg Lys Gly Gly Ser Tyr Ser Gln Ala Ala Ser Ser Asp Ser
            340                 345                 350 gcc cag ggc tct gat gtg tct ctc aca gct tgt aaa gtg tga              1098
Ala Gln Gly Ser Asp Val Ser Leu Thr Ala Cys Lys Val
        355                 360                 365

<210> SEQ ID NO 8
<211> LENGTH: 365
<212> TYPE: PRT
<213> ORGANISM: Homo sapiens

<400> SEQUENCE: 8

Met Ala Val Met Ala Pro Arg Thr Leu Val Leu Leu Leu Ser Gly Ala
1               5                   10                  15

Leu Ala Leu Thr Gln Thr Trp Ala Gly Ser His Ser Met Arg Tyr Phe
            20                  25                  30

Tyr Thr Ser Val Ser Arg Pro Gly Arg Gly Glu Pro Arg Phe Ile Ala
        35                  40                  45

Val Gly Tyr Val Asp Asp Thr Gln Phe Val Arg Phe Asp Ser Asp Ala
    50                  55                  60

Ala Ser Gln Arg Met Glu Pro Arg Ala Pro Trp Ile Glu Gln Glu Gly
65                  70                  75                  80

Pro Glu Tyr Trp Asp Gly Glu Thr Arg Lys Val Lys Ala His Ser Gln
                85                  90                  95

Thr His Arg Val Asp Leu Gly Thr Leu Arg Gly Tyr Tyr Asn Gln Ser
            100                 105                 110

Glu Ala Gly Ser His Thr Val Gln Arg Met Tyr Gly Cys Asp Val Gly
        115                 120                 125

Ser Asp Trp Arg Phe Leu Arg Gly Tyr His Gln Tyr Ala Tyr Asp Gly
    130                 135                 140

Lys Asp Tyr Ile Ala Leu Lys Glu Asp Leu Arg Ser Trp Thr Ala Ala
145                 150                 155                 160

Asp Met Ala Ala Gln Thr Thr Lys His Lys Trp Glu Ala Ala His Val
                165                 170                 175

Ala Glu Gln Leu Arg Ala Tyr Leu Glu Gly Thr Cys Val Glu Trp Leu
            180                 185                 190

Arg Arg Tyr Leu Glu Asn Gly Lys Glu Thr Leu Gln Arg Thr Asp Ala
        195                 200                 205

Pro Lys Thr His Met Thr His His Ala Val Ser Asp His Glu Ala Thr
    210                 215                 220

Leu Arg Cys Trp Ala Leu Ser Phe Tyr Pro Ala Glu Ile Thr Leu Thr
225                 230                 235                 240
```

-continued

```
Trp Gln Arg Asp Gly Glu Asp Gln Thr Gln Asp Thr Glu Leu Val Glu
                245                 250                 255
Thr Arg Pro Ala Gly Asp Gly Thr Phe Gln Lys Trp Ala Ala Val Val
                260                 265                 270
Val Pro Ser Gly Gln Glu Gln Arg Tyr Thr Cys His Val Gln His Glu
            275                 280                 285
Gly Leu Pro Lys Pro Leu Thr Leu Arg Trp Glu Pro Ser Ser Gln Pro
            290                 295                 300
Thr Ile Pro Ile Val Gly Ile Ile Ala Gly Leu Val Leu Phe Gly Ala
305                 310                 315                 320
Val Ile Thr Gly Ala Val Val Ala Ala Val Met Trp Arg Arg Lys Ser
                325                 330                 335
Ser Asp Arg Lys Gly Gly Ser Tyr Ser Gln Ala Ala Ser Ser Asp Ser
                340                 345                 350
Ala Gln Gly Ser Asp Val Ser Leu Thr Ala Cys Lys Val
                355                 360                 365
```